US011065403B2

(12) United States Patent
Yoch et al.

(10) Patent No.: US 11,065,403 B2
(45) Date of Patent: Jul. 20, 2021

(54) BLISTER STRIP ADVANCE MECHANISM

(71) Applicant: MicroDose Therapeutx, Inc., Monmouth Junction, NJ (US)

(72) Inventors: Travis Ernest Yoch, Woodbury, MN (US); Robert R. Roberts, III, St. Paul, MN (US)

(73) Assignee: MICRODOSE THERAPEUTX, INC., Monmouth Junction, NJ (US)

( * ) Notice: Subject to any disclaimer, the term of this patent is extended or adjusted under 35 U.S.C. 154(b) by 685 days.

(21) Appl. No.: 15/094,094

(22) Filed: Apr. 8, 2016

(65) Prior Publication Data

US 2016/0296717 A1  Oct. 13, 2016

Related U.S. Application Data

(60) Provisional application No. 62/145,923, filed on Apr. 10, 2015.

(51) Int. Cl.
*A61M 15/00* (2006.01)

(52) U.S. Cl.
CPC .... *A61M 15/0051* (2014.02); *A61M 15/0025* (2014.02); *A61M 15/0091* (2013.01);
(Continued)

(58) Field of Classification Search
CPC .............. A61M 15/00; A61M 15/0025; A61M 15/0051; A61M 15/0091; A61M 15/0001;
(Continued)

(56) References Cited

U.S. PATENT DOCUMENTS

| 5,119,969 | A | * | 6/1992 | Haber | A61J 7/0076 |
|           |   |   |        |       | 221/25 |
| 5,590,645 | A | * | 1/1997 | Davies | A61M 15/0045 |
|           |   |   |        |        | 128/203.15 |

(Continued)

FOREIGN PATENT DOCUMENTS

| CA | 2893558 | 6/2014 |
| CN | 1054893 A | 10/1991 |

(Continued)

OTHER PUBLICATIONS

International Search Report and Written Opinion of the International Searching Authority for International Application No. PCT/US2016/026593 dated Jun. 29, 2016, 10 pages.

(Continued)

*Primary Examiner* — Justine R Yu
*Assistant Examiner* — Matthew D Ziegler
(74) *Attorney, Agent, or Firm* — Morgan, Lewis & Bockius LLP

(57) ABSTRACT

A blister strip advance mechanism includes: an indexing gear train; drive mechanism configured to drive the indexing gear train; and a hub including a recess shaped to engage a first blister of a blister strip, the hub being rotatable by the indexing gear train to engage the first blister in the recess and move the engaged blister strip such that a second blister is moved to a dosing position at which the second blister can be emptied; wherein the indexing gear train is configured to temporarily disengage the drive mechanism from the hub when the second blister is in the dosing position. Also disclosed is a dosing mechanism including the blister strip advance mechanism; an inhaler including the dosing mechanism; a method for advancing a blister strip; and a method for dosing a medicament including the method for advancing a blister strip.

41 Claims, 25 Drawing Sheets

(52) U.S. Cl.
CPC . *A61M 2202/064* (2013.01); *A61M 2205/502* (2013.01); *A61M 2205/8206* (2013.01)

(58) Field of Classification Search
CPC .......... A61M 15/0021; A61M 15/0028; A61M 15/0045; A61M 15/0046; A61M 15/0053; A61M 15/0058; A61M 15/0043; A61M 2202/064; A61M 2205/502; A61M 2205/8206; A61M 2205/10; A61M 2205/103; A61M 2205/19; B65H 20/02
USPC .................................. 221/25, 30–32, 69–71
See application file for complete search history.

(56) References Cited

U.S. PATENT DOCUMENTS

| | | | | |
|---|---|---|---|---|
| 5,619,984 | A * | 4/1997 | Hodson | A61M 15/0028 128/203.12 |
| 6,318,437 | B1 * | 11/2001 | Yoo | H05K 13/0419 156/750 |
| 6,379,098 | B1 * | 4/2002 | Shibasaki | H05K 13/0419 414/416.01 |
| 6,439,289 | B1 * | 8/2002 | Schlotthauer | B65C 9/0006 156/539 |
| 10,188,810 | B2 | 1/2019 | Meliniotis et al. | |
| 10,434,267 | B2 | 10/2019 | Akouka et al. | |
| 2003/0172927 | A1 * | 9/2003 | Young | A61M 15/0045 128/203.15 |
| 2004/0094152 | A1 * | 5/2004 | Harvey | A61M 15/0045 128/203.15 |
| 2004/0099676 | A1 | 5/2004 | Anderson et al. | |
| 2005/0268909 | A1 | 12/2005 | Bonney et al. | |
| 2007/0131225 | A1 * | 6/2007 | Rand | A61M 15/0028 128/200.23 |
| 2007/0181123 | A1 * | 8/2007 | Houzego | A61M 15/0045 128/203.15 |
| 2008/0022998 | A1 | 1/2008 | Hamano et al. | |
| 2010/0294278 | A1 | 11/2010 | Mosier | |
| 2011/0162642 | A1 | 7/2011 | Akouka | |
| 2012/0138055 | A1 * | 6/2012 | Meliniotis | A61M 15/0045 128/203.15 |
| 2015/0174345 | A1 * | 6/2015 | Toksoz | A61M 15/0043 128/203.15 |
| 2015/0297841 | A1 | 10/2015 | Ono | |

FOREIGN PATENT DOCUMENTS

| | | | | |
|---|---|---|---|---|
| CN | 103429288 | A | 12/2013 | |
| EP | 2666498 | A1 * | 11/2013 | ........ A61M 15/0045 |
| GB | 2485858 | | 5/2012 | |
| JP | 2004-512146 | A | 4/2004 | |
| JP | 2005-533584 | A | 11/2005 | |
| JP | 2013-516283 | A | 5/2013 | |
| JP | 2013-544170 | A | 12/2013 | |
| JP | 2014-113260 | A | 6/2014 | |
| TW | 200906456 | A | 2/2009 | |
| WO | 0236188 | A2 | 5/2002 | |
| WO | 2004011070 | A1 | 2/2004 | |
| WO | 2008145348 | A2 | 4/2008 | |
| WO | 2008058964 | | 5/2008 | |
| WO | WO-2010114506 | A1 * | 10/2010 | ........ A61M 15/0045 |
| WO | 2011085022 | A1 | 7/2011 | |
| WO | 2012069854 | A2 | 5/2012 | |
| WO | 2013176643 | A1 | 11/2013 | |
| WO | 2014088055 | A1 | 12/2014 | |
| WO | 2016164689 | A1 | 10/2016 | |

OTHER PUBLICATIONS

Eurasian Office Action for Application No. 201792225/31; dated Sep. 4, 2019; 2 pages.
English translation of Eurasian Office Action for Application No. 201792225/31; dated Sep. 4, 2019; 2 pages.
Chinese First Office Action for Chinese Patent Application No. 201680026421.9, 12 pages.
Japanese Office Action dated Feb. 19, 2020 for Japanese Patent Application No. 2017552977, 9 pages.
Argentina Office Action for Argentina Patent Application No. P160100905, 6 pages.
Chinese Office Action dated Oct. 30, 2020 for Chinese Patent Application No. 201680026421.9, 5 pages.
Australian Examination Report No. 1 dated Feb. 4, 2020 for Australian Patent Application No. 2016244872, 4 pages.
Office Action dated Feb. 12, 2019 for Eurasian Patent Application No. 201792225/31, 4 pages.
Official Action dated Oct. 1, 2020 for Mexican Patent Application No. MX/a/2017/012799, 4 pages with English translation.
Office Action dated Dec. 26, 2016 for Taiwan Patent Application No. 105109902, 10 pages.
Japanese Decision of Refusal for JP 2017-552977; dated Nov. 13, 2020; 2 pages.
English translation of Japanese Decision of Refusal for JP 2017-552977; dated Nov. 13, 2020; 2 pages.
Israel Office Action for IL 254776; dated Jan. 19, 2021; 3 pages.

* cited by examiner

BLISTER STRIP ADVANCE MECHANISM

CROSS-REFERENCE TO RELATED APPLICATIONS

This application is a U.S. Non-Provisional Patent Application, which claims priority of U.S. Provisional Patent Application No. 62/145,923, filed Apr. 10, 2015, which is incorporated by reference herein in its entirety.

FIELD OF THE INVENTION

The present disclosure generally relates to a mechanism for advancing a strip of blisters (for example containing a pharmaceutical composition) one by one, such as may be required for administering individual doses of medicament to the user of an inhaler.

BACKGROUND OF THE INVENTION

Metred dose inhalers (MDIs) are multiple use devices for delivering drugs to the airways of patients suffering from respiratory complaints. It is important to ensure the correct quantity of drug is administered since enough must be delivered to have the desired medicinal effect but excessive quantities can be dangerous. This can be achieved with metering mechanisms to measure drug out of a hopper or reservoir, or by encasing individual doses of drug in capsules or blisters. The latter approach is particularly useful in dry powder inhalers (DPIs).

Where blisters are used, it is desirable for a mechanism to be provided to advance a blister strip, drum or cartridge one blister at a time since manual blister advance may be onerous for a user who may lack the required dexterity. This is even more important for rescue inhalers used in response to an acute respiratory event such as an asthma attack, when the user may not be able to concentrate enough to complete a manual dose advance.

One previously proposed blister advance mechanism is described in United States patent application publication number 2010/0294278, which incorporated by reference herein. This publication describes an inhaler with a rotary blister cassette having blisters arranged around the circumference of a wheel. The wheel rotates against a ratchet so that it advances one blister at a time, and always in the same direction so that adjacent blisters are used in sequence until the cartridge is empty. Uncovering of a mouthpiece and indexing of the wheel are both achieved by movement of a lever arm linked to the wheel by a cam disc.

Such a purely mechanical mechanism is effective, but it may be desirable for blisters to be advanced under electronic control, for example so that blister advance can be in response to sensing of particular conditions e.g. blister advance may be responsive to user inhalation through a mouthpiece. (This has the advantage of only exposing the drug at the time the patient is using the device. In contrast, if a manual approach is used, the user could be interrupted between dose advance and inhalation, leaving the drug exposed for a long period of time.)

Therefore a blister advance mechanism comprising some non-user-actuated drive means, such as a motor, may be preferred. United States patent application publication number 2011/0162642, which is incorporated by reference herein, for example describes an inhaler having a blister strip arranged in a disposable cartridge wherein the blister strip is advanced by a motor. A blister detection switch is proposed to sense the advancement of the blister strip and facilitate controlling the advancement of the blister strip to consistently position individual blisters relative to an aerosol chamber into which the blisters' content is released for delivery to a patient.

However, it may be difficult to control the motor accurately enough with such a switch to ensure that under- and over-advancement of the blister strip is always prevented.

The potential for misalignment of the blister with the dosing chamber reduces predictability of an inhaler since it is not possible to be sure the entire dose is emptied from the blister. If the full dose is not delivered the effectiveness of the treatment may be compromised. A further effect can be that the patient does not respond to treatment as well as expected. Their doctor could then increase the prescribed dose to a level which is not necessarily safe for that patient on occasions when the blister happens to be correctly aligned, or which at least wastes medicament.

If the blister strip overshoots the opening, the following blister may be inadvertently (partially) opened, for example if too much of a blister backing strip is peeled. This can compromise the next dose, both in quantity (since some drug may leak from the blister) and quality (since some drugs have limited stability when exposed to air).

An alternative blister strip advance mechanism is therefore needed.

SUMMARY OF THE INVENTION

According to a first aspect, there is provided a blister strip advance mechanism comprising: an indexing gear train; drive means configured to drive said indexing gear train; and a hub comprising a recess shaped to engage a first blister of a blister strip. Said hub is rotatable by the indexing gear train to engage the first blister in said recess and move the engaged blister strip such that a second blister is moved to a dosing position at which the second blister can be emptied. The indexing gear train is configured to temporarily disengage said drive means from the hub when the second blister is in said dosing position.

The indexing gear train could comprise a sector gear.

The indexing gear train could further comprise a spur gear, the hub being arranged to be driven by said spur gear, the spur gear being arranged to be driven by said sector gear and the sector gear being arranged to be driven by the drive means.

Said sector gear could be the blocking disc of a Geneva drive and said hub could be, or could be driven by, a Maltese gear of a Geneva drive.

The hub could be further rotatable by the indexing gear train to release the first blister. The hub could be further rotatable by the indexing gear train to engage the second blister.

The blister strip advance mechanism could further comprise a track through which said blister strip can move. Part of said track could pass around part of the hub's circumference such that the second blister can be engaged by the hub when the blister strip is in the track. The track could be shaped such that, as the blister strip is advanced, its leading end moves into a part of the track vacated by the blister strip's trailing end.

Said track could comprise a biasing means, such as a spring finger arranged to bias the blister against the wall of the dose tunnel thus holding a blister in the dosing position when the drive means is disengaged from the hub. This ensures the seal of the blister to the dose tunnel and helps prevent loss of powder into the cartridge.

The blister strip advance mechanism could further comprise a peeling/spooling gear carrying a spool arranged to rotate therewith and to which an end of a backing strip of the blister strip can be affixed. Said peeling/spooling gear could be configured to be rotated by the indexing gear train substantially concurrently with the hub such that backing is peeled off the second blister via a peel edge as it is moved into the dosing position, arrival of the second blister at the dosing position being substantially coincident with completion of peeling of backing from the second blister.

The peeling/spooling gear could be arranged to be driven by the sector gear.

The peeling/spooling gear could be arranged with respect to the hub such that, in operation, backing is peeled off the second blister at an angle of between 40 and 140 degrees.

The blister strip advance mechanism could further comprise a slip clutch on the peeling/spooling gear.

The indexing gear train could comprise a worm gear carried on an output shaft of the drive means and arranged to rotate therewith. The indexing gear train could comprise a first spur gear meshing with said worm gear. The indexing gear train could comprise a first sector gear carried on said first spur gear and arranged to rotate therewith. The indexing gear train could comprise a second spur gear meshing with said first sector gear. The indexing gear train could comprise a second sector gear carried on said second spur gear and arranged to rotate therewith. The indexing gear train could comprise a third sector gear meshing with said second sector gear. The peeling/spooling gear could be a third spur gear meshing with the first sector gear. The hub could be carried on the third sector gear and could be arranged to rotate therewith.

The blister strip advance mechanism could further comprise one or more detents arranged to hold the indexing gear train in position when it is disengaged from the drive means. Said one or more detents could be comprised in a fixed cover. Said one or more detents could each be located on the distal end of a spring arm. Said one or more spring arms could be biased towards one or more recesses. Said one or more recesses could be located on one or more moveable components of the drive train.

According to a second aspect there is provided a dosing mechanism comprising: the blister strip advance mechanism of the first aspect; and a dosing chamber comprising two openings, the dosing position being aligned with one of said openings such that contents of the blister in the dosing position can only exit the blister via said dosing chamber. The other opening whereby the medicament exits the dosing chamber into the dose channel may comprise one or multiple openings, for example 2, 3, 4 or 5 or more openings, as necessary.

According to a third aspect there is provided an inhaler comprising the dosing mechanism of the second aspect.

The inhaler could comprise an inhaler body and a replaceable blister strip cartridge. Said inhaler body could comprise the dosing chamber, the drive means, the indexing gear train and the hub. Said replaceable blister strip cartridge could comprise the blister strip.

According to a fourth aspect there is provided a method for advancing a blister strip comprising: engaging a first blister of said blister strip in a recess of a hub; rotating said hub by means of an indexing gear train driven by drive means to move a second blister of the blister strip to a dosing position at which said second blister can be emptied; and temporarily disengaging said drive means from said hub when the second blister is in said dosing position.

The method could further comprise further rotating the hub by the indexing gear train to release the first blister. The method could further comprise further rotating the hub by the indexing gear train to engage the second blister. The method could further comprise the leading end of the blister strip moving into a part of a track through which said blister strip is moving already vacated by the blister strip's trailing end as the blister strip advances. Part of said track could pass around part of the hub's circumference such that the blister is engaged by the hub when the blister strip is in the track.

The method could further comprise the indexing gear train rotating a peeling/spooling gear carrying a spool arranged to rotate therewith and to which an end of a backing strip of the blister strip is affixed. Said rotation of said peeling/spooling gear could be substantially concurrent with said rotation of the hub such that backing is peeled off the second blister via a peel edge as it is moved into the dosing position, arrival of the second blister at the dosing position being substantially coincident with completion of peeling of backing from the second blister.

The method could further comprise rotating an output shaft of the drive means such that a worm gear carried on said output shaft rotates therewith; such that a first spur gear meshing with said worm gear rotates therewith; such that a first sector gear carried on said first spur gear rotates therewith; such that the peeling/spooling gear, being a third spur gear meshing with the first sector gear, rotates therewith; and such that a second spur gear meshing with said first sector gear rotates therewith; such that a second sector gear carried on said second spur gear rotates therewith; such that a third sector gear meshing with said second sector gear rotates therewith; such that the hub, being carried on the third sector gear, rotates therewith.

According to a fifth aspect there is provided a method for dosing a medicament, such as a dry powder medicament, comprising: the method of the fourth aspect; and emptying contents of the second blister into a dosing chamber comprising two openings, the dosing position being aligned with one of said openings such that contents of the second blister in the dosing position can only exit the second blister via said dosing chamber. The other opening whereby the medicament exits the dosing chamber into the dose channel may comprise one or multiple openings, for example 2, 3, 4 or 5 or more openings, as necessary.

BRIEF DESCRIPTION OF THE DRAWINGS

Examples of the present invention will now be described with reference to the accompanying drawings, in which.

DETAILED DESCRIPTION OF THE INVENTION

Figure 1A:
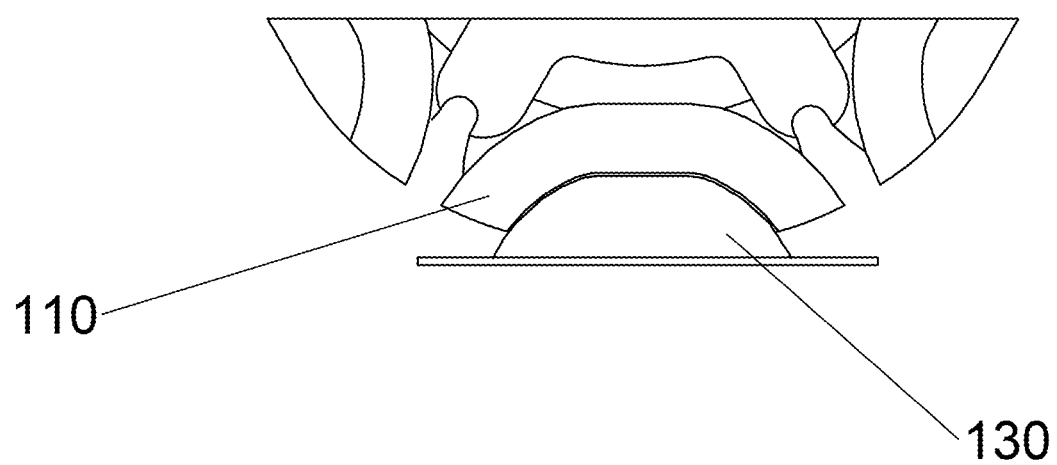
FIGS. 1A, 1B, 1C, 1D, 1E, 1F, 1G and 1H illustrate example hub arrangements and examples of how a blister may be held in a dosing position.

One way of preventing over-advancement of a blister strip is to employ mechanical indexing means, such as the indexing gear train proposed herein.

Such an indexing gear train is driven by drive means such as an electric motor e.g. a stepper or DC (direct current) motor. The drive means may be under electronic control to switch it on and off in order to advance the blister strip by one blister. This electronic control may be responsive to user input or to sensing means (such as a mechanical switch) configured to sense when a blister has been successfully located in a dosing position at which it can be emptied. For example, the dosing position may correspond to the entrance to a dosing chamber into which medicament (such as a dry powder pharmaceutical) contained in the blister must be released so that it can be entrained in a user's inhalation and delivered into their airway. For example, a dry powder medicament may be expelled from the inhaler in artificial jets by excitation of a piezoelectric drum during inhalation.

At the other end of the gear train to the drive means a hub is provided with at least one recess, each configured to engage a single (first) blister of a blister strip so that another (second) blister of the strip can be moved into a dosing position and optionally held against the dose tunnel wall with biasing means. Thus, the hub holds the blister strip in place with a (second) blister in the dosing position and an empty (first) blister in the hub, while the (second) blister in the dosing position is emptied. Thus, in this example arrangement, the hub and dosing chamber opening are arranged one blister spacing apart. The (second) blister in the dosing position is arranged such that there is a tight seal between the blister cup walls and the dosing chamber walls so that medicament from the blister can only exit into the dosing chamber. This prevents wastage of medicament and clogging of the mechanism with medicament. Optional biasing means (spring finger 172 in FIG. 1H) can be incorporated to improve the seal.

The drive train is arranged such that, once a second blister arrives at the dosing position, the drive means is temporarily disengaged from the hub. This means that, provided the indexing gear train is configured to make this temporary disengagement last as long or longer than the time taken for the electronic control system to receive and respond to a signal indicating that the second blister is in the dosing position, over-advancement of the blister strip is avoided. This reduces the need for high motor speed and control accuracy, since there is a large window within which to stop the motor in order to not over- or under-advance the blister. This also prevents inadvertent movement of the blister strip if the cartridge is removed in between dose events.

The mechanism for temporarily disengaging the hub from the drive means may comprise one or more spur gears and one or more sector gears. A spur gear comprises radially extending teeth substantially evenly spaced all the way around its circumference. A sector gear is effectively a spur gear with the teeth missing from one or more portions of the circumference. When a rotating sector gear drives a spur gear, the spur gear is only driven while the toothed portion(s) of the sector gear engage it. When a toothless portion of the sector gear comes into contact with the teeth of the spur gear, the spur gear stops rotating. The sector gear continues to rotate until a toothed portion contacts and engages with the teeth of the spur gear. The spur and sector gears then rotate together until a toothless portion of the sector gear contacts the spur gear again. Therefore, if rotation of the hub is driven by a spur gear, temporary disengagement of the hub from the drive means can be provided if the drive means drives a sector gear which in turn drives the spur gear which in turn drives the hub.

Figure 1B:
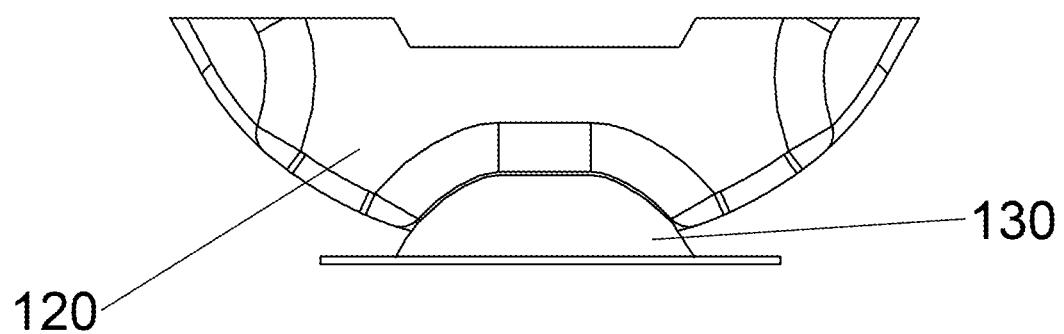
Figure 1C:
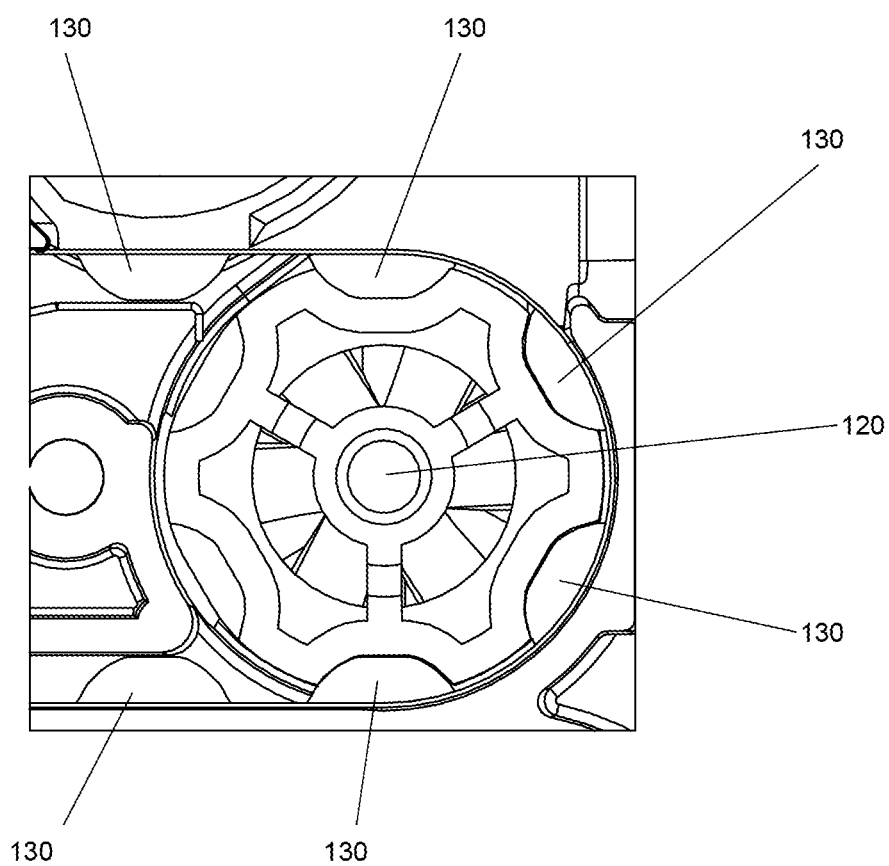
Figure 1D:
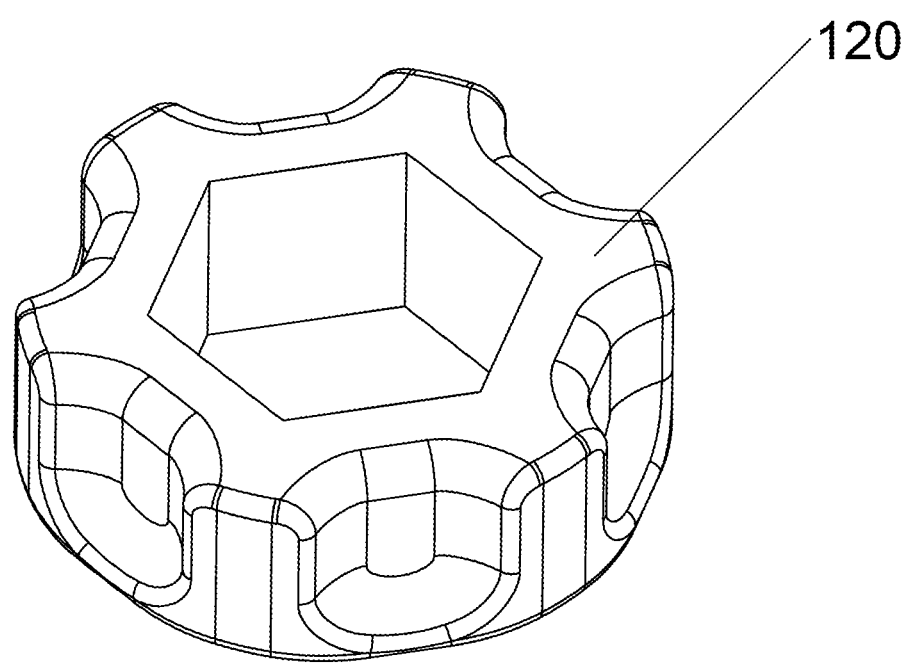
Figure 1E:
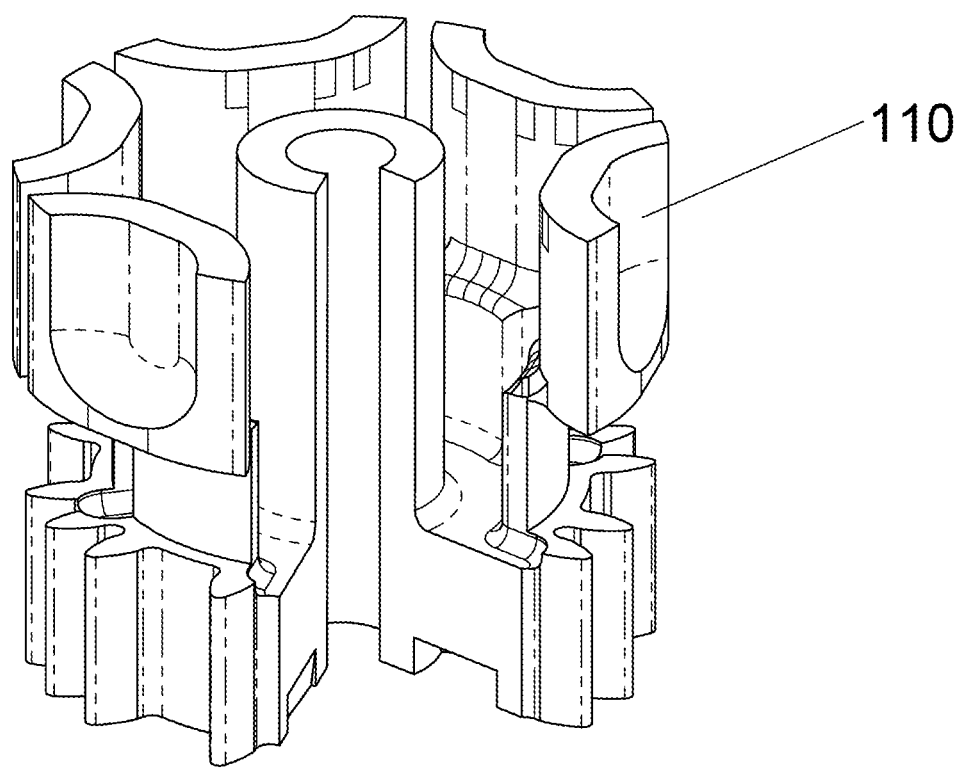

The hub may, for example, be in the form of an involute cog 110 as shown in FIG. 1A or an offset cog 120 as shown in FIG. 1B. By "involute cog" is intended an open type of blister seat in the hub such that the blister strip will twist in to the seat of the cog, and then twist out (much like the fashion in which involute gear teeth engage as they come together to a point of tangency and then pivot away from one another). By "offset cog" is intended a cut out arrangement where the blister strip wraps around the hub with the empty blisters engaging with the recesses on the hub without twisting of the strip; this is the arrangement illustrated in FIG. 4A. The recesses formed around the circumference of either shape cog can be sized to receive a single blister 130 of the blister strip to be advanced. Advantageously, the offset cog profile does not tend to misalign or crush blisters or cause the blister strip to buckle. FIG. 1C illustrates an example hub 120 in use. In this example, the track through which the blister strip moves passes around about half the circumference of the hub so that multiple blisters 130 are engaged by the hub at once. FIGS. 1D and 1E illustrate alternative example designs for hub 120.

Figure 1F:
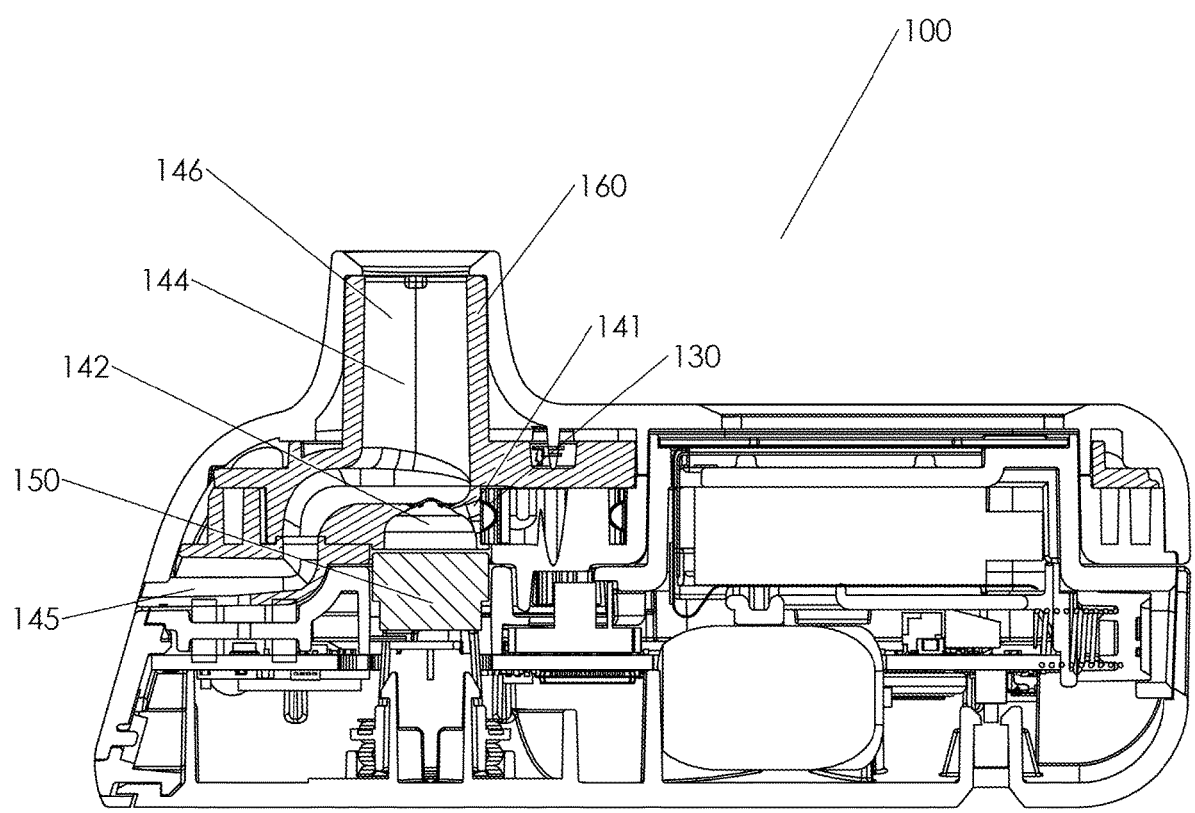
Figure 1G:
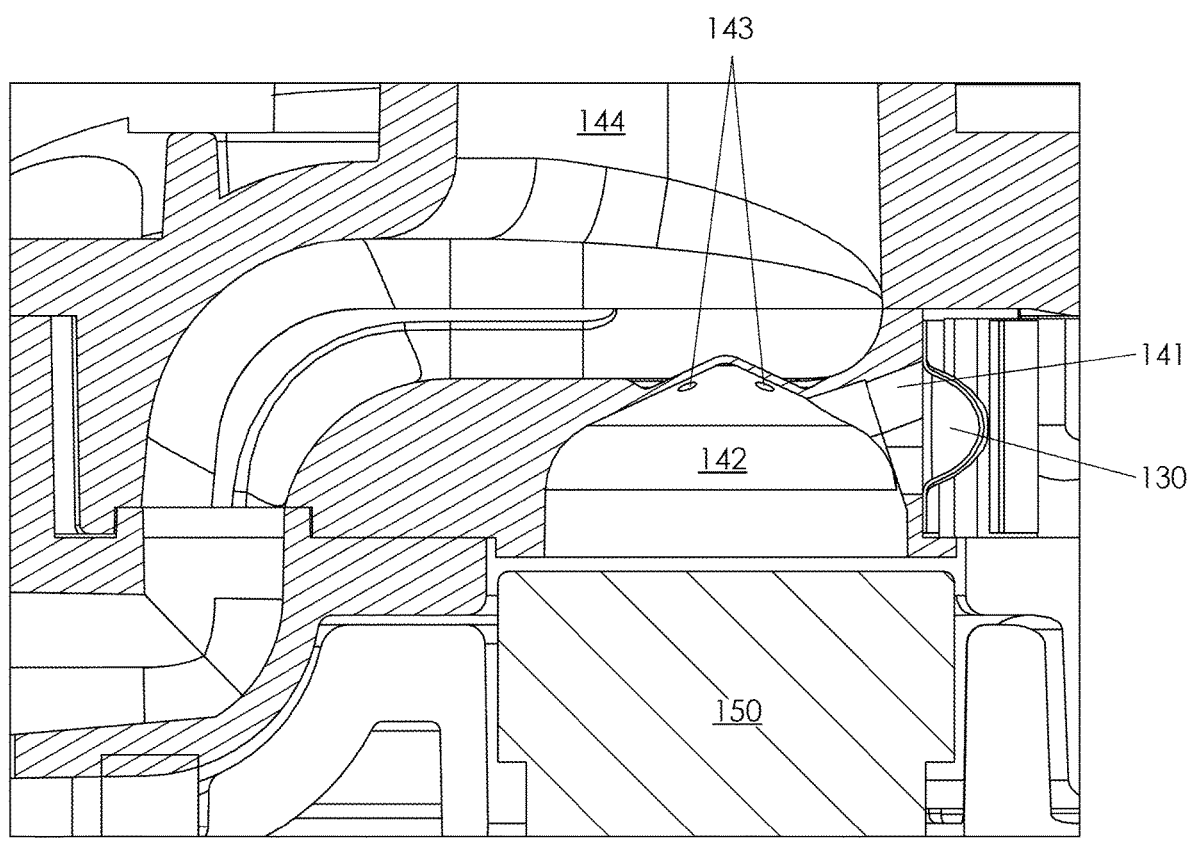

FIGS. 1F and 1G (which shows detail on FIG. 1F) illustrate an example of how the blister dosing position could be arranged with respect to other elements of an inhaler 100. Blister 130 is shown in the dosing position, with its open (peeled) side facing on to blister dose tunnel 141 which pneumatically connects the dosing position to dose chamber 142. Piezoelectric vibrator 150 is arranged to vibrate a film, that is in contact with the edge of the dose chamber 142 bottom, which is in contact with the Piezoelectric vibrator 150 head, such that dry powder medicament contained in the blister 130 and dosing chamber 142 is expelled from the dosing chamber through holes 143 into air tunnel 144. Thus, the vibration acts as a percussion on the film, much like a drum. The medicament is thus entrained in airflow from inlet 145 through air tunnel 144 and out of outlet 146 in mouthpiece 160.

Figure 1H:
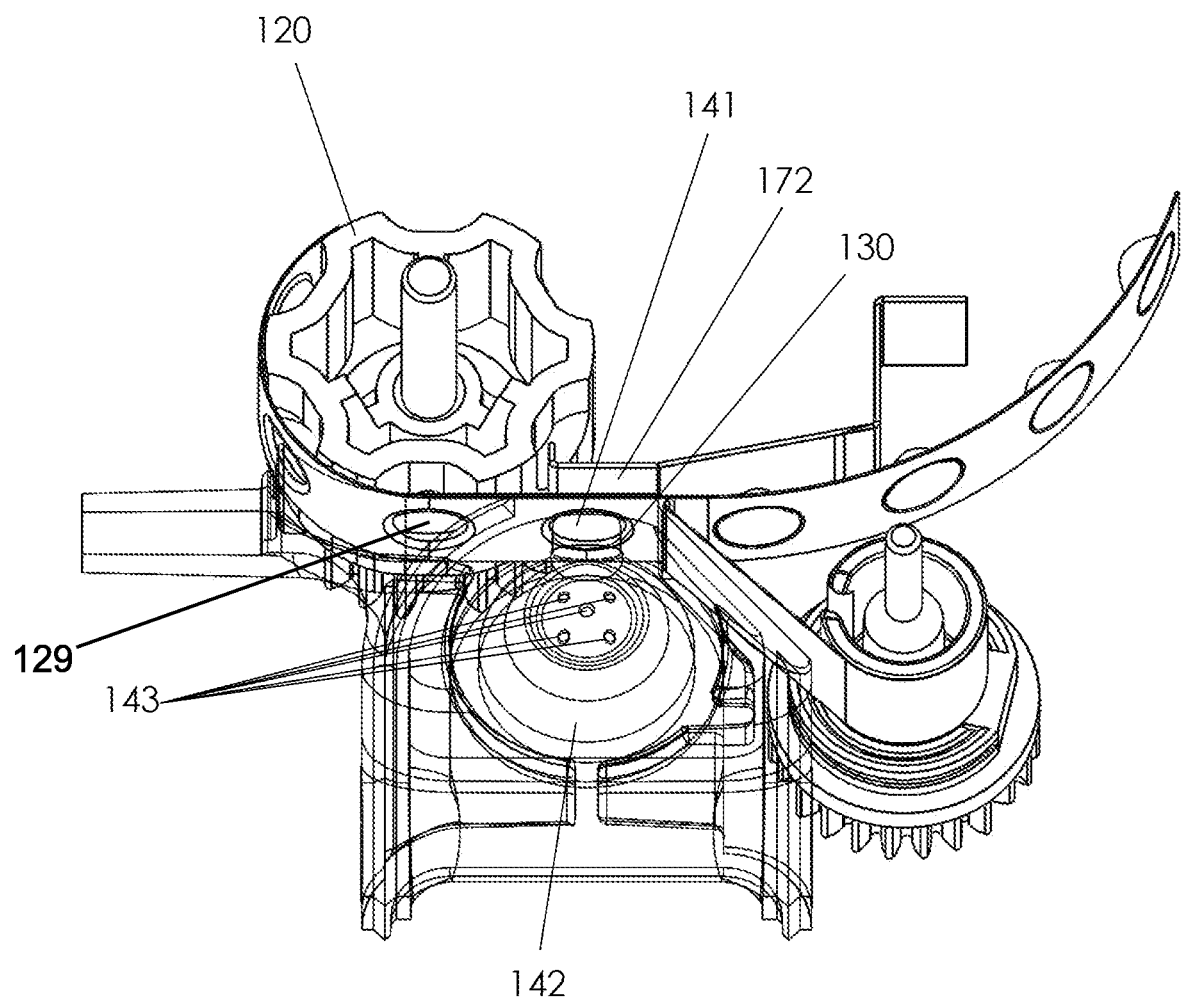

FIG. 1H shows a different view on FIGS. 1F and 1G, with the dosing position shown relative to hub 120. First blister 129 is held in the hub. Also shown is spring finger 172 which biases the second blister 130 towards dose chamber tunnel 141. This, in combination with the fact that the dosing position holds the open face of second blister 130 approximately horizontal in use, with the hollow part extending downwards, minimises spillage of medicament from the blister other than into the tunnel 141.

The blister strip advance mechanism may be configured to incrementally move successive blisters of a blister strip through the dosing position. That is, once the second blister has been moved into the dosing position and emptied, the hub can be rotated such that the empty second blister is engaged by the hub and a third (full) blister is moved into the dosing position and so on until every blister on the strip has been emptied, empty blisters being released from the hub at a suitable point before they have completed a full hub rotation.

Once the second blister has been emptied, the leading end of the strip (comprising the first, empty, blister) may be fed out of the inhaler where it could for example be cut off with scissors, or torn off (e.g. using a tearing notch or a score line or perforation in the strip between blisters) and disposed of. If individual blisters are only held together as a strip by the backing tape then no cutting or tearing would be necessary. Alternatively, the inhaler could comprise a waste chamber into which used blisters are fed. The used blister strip sections could, for example, accordion-fold into such a chamber, or be wound onto a spool.

As another option, if the blister strip is short enough relative to the inhaler geometry, a single loop track could be provided with the hub positioned anywhere inside it, the hub's teeth extending into the track. This would allow used blisters to be stored within the inhaler and disposed of with the inhaler when all of the blisters are used (or with the cartridge if a replaceable blister cartridge is provided for attachment to a reusable inhaler body). In such an arrangement the leading end of the strip could be fed into a refuse track within the inhaler. This track could be an extension of a holding track in which the blister strip is stored prior to use and in which the trailing end of the strip (comprising one or more full blisters) reside during advancement of the strip. The refuse track could loop around into the holding track, the dual track being formed thereby being sized and arranged such that the leading end of the blister strip is fed into a portion of the dual track vacated by the trailing end.

Figure 2A:
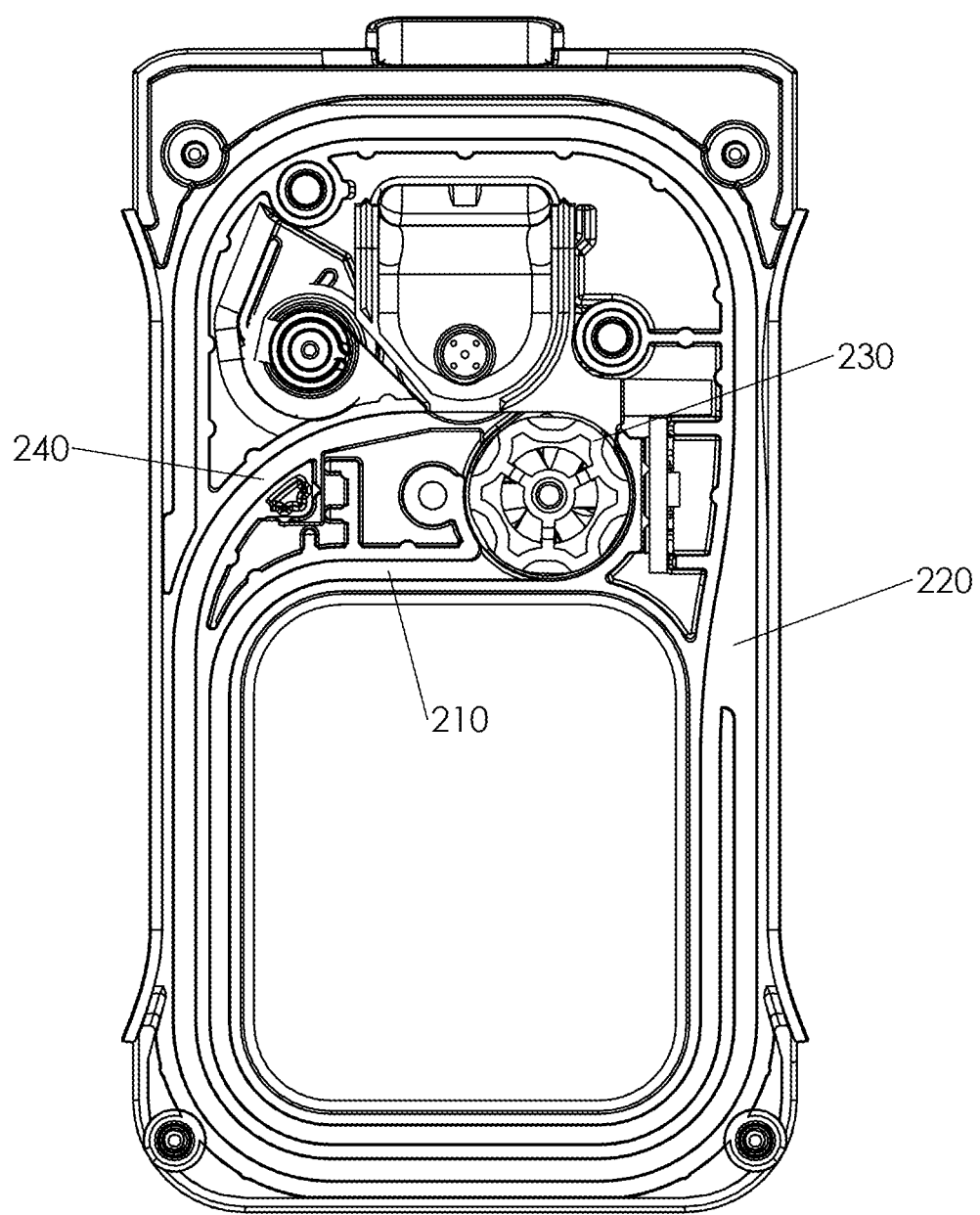
FIGS. 2A, 2B and 2C illustrate example blister strip tracks.

A variant of the dual track arrangement is illustrated in FIG. 2. This variant reduces the required footprint of the track for the same length of blister strip relative to the single loop variant and thus potentially reduces the size of the inhaler/cartridge and/or increases its blister capacity. Since some inhalers (e.g. rescue inhalers and frequent use inhalers) must be carried at all times this is advantageous since it improves the inhaler's portability. Shown in FIG. 2A is a holding track 240 fed by a dual track 220. The holding track 240 approaches and follows a portion of the circumference of hub 230 and then becomes refuse track 210. Refuse track 210 then leads back into dual track 220.

Figure 2B:
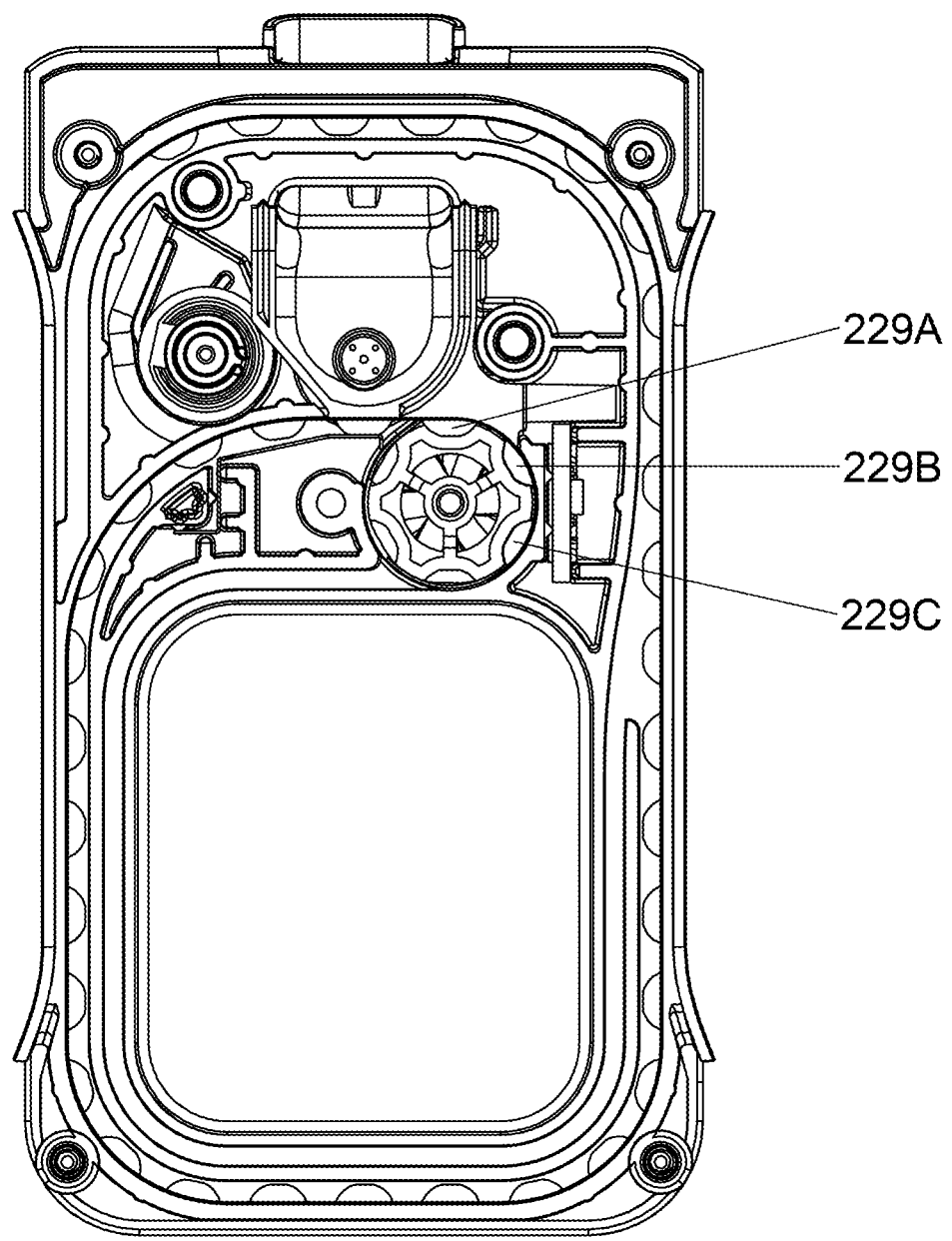
Figure 2C:
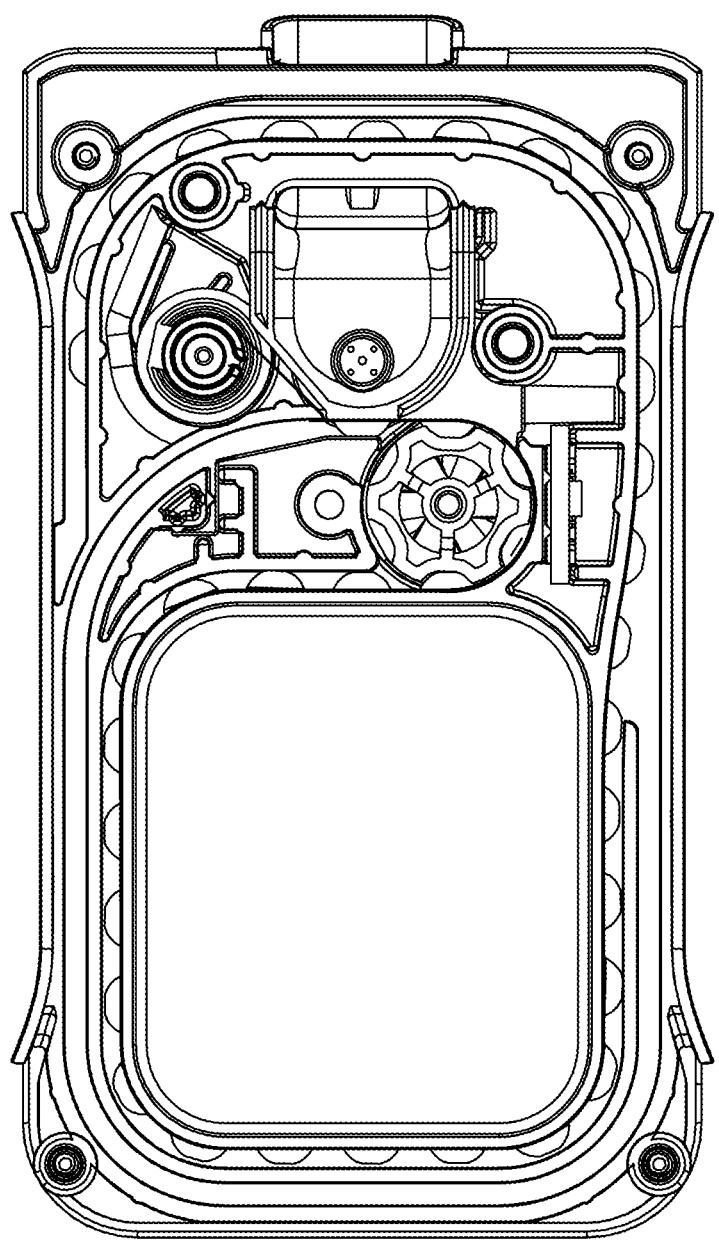

FIGS. 2B and 2C illustrate another similar blister strip track. The initial position of the blister strip is shown in FIG. 2B and the final position of the blister strip (when all blisters have been emptied) in FIG. 2C.

As shown in FIG. 2B, in addition to first blister 229a, the hub also engages blisters 229b and 229c in the starting position to improve engagement of the blister strip as a whole. Any blisters engaged by the hub in the starting position may suitably be provided empty to avoid medicament spilling around the hub or into the refuse track.

Alternatively to a dual track arrangement, the blister strip may be stored on a spool from which it is incrementally unwound.

The blister strip may be formed of a plurality of relatively rigid (e.g. plastic or aluminium) domes or cups connected and enclosed by a strip of backing tape (sometimes known as lidding material). Medicament (e.g. in liquid or dry powder form) may be enclosed in the cups. Individual blisters may be opened by piercing the backing tape, the dome or both. Alternatively, blisters may be opened by peeling away the backing tape.

If the backing tape is peeled to open the blisters, a spool may be provided around which to wind peeled backing tape. Such a spool may be carried on a peeling/spooling gear. The leading end of the blister strip may comprise a lip of backing tape or a tab extending out past the distal end of the distal blister cup. This lip or tab can be affixed to the spool. The peeling/spooling gear can be rotated by the indexing gear train while the hub is rotated so that backing is peeled off each blister and wound around the spool as the blister cup is moved into the dosing position. The blister cup is therefore open when in the dosing position, making medicament available to the dosing chamber.

To ensure the timing of the peeling matches the timing of the blister cup being moved into the dosing position, the peeling/spooling gear can be driven by a gear (e.g. a sector gear) that also (directly or indirectly) drives the hub.

The peeling/spooling gear and the hub can be located such that backing is peeled off each blister cup at an angle close to a right angle to the backing remaining on the blister cup, for example at between 40 and 140° (e.g. 135°), for example at between 60 and 120°, for example at approximately 90°. The closer the peel angle to 90°, the lower the friction between the backing tape and the edge it is peeled off with. Reducing friction reduces motor load, thus saving power, and reduces the likelihood of the backing strip breaking.

Figure 3A:
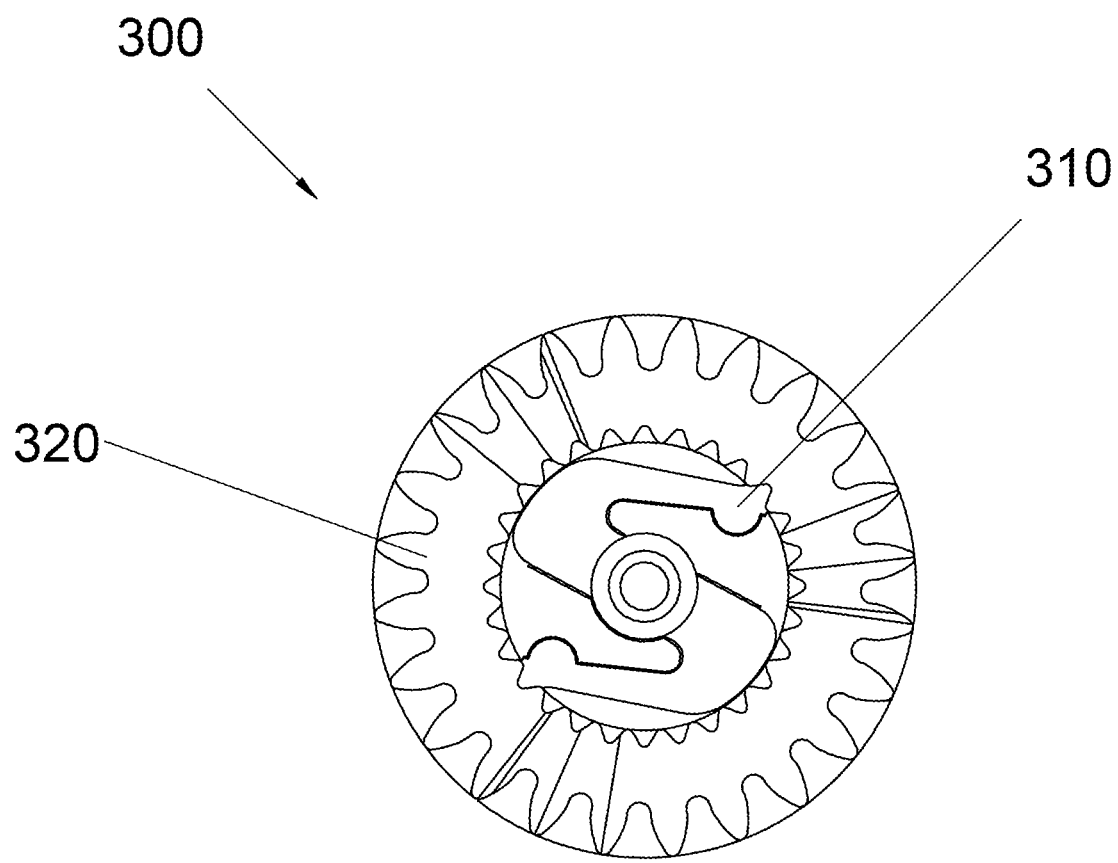
FIGS. 3A and 3B illustrate an example detent clutch.
Figure 3B:
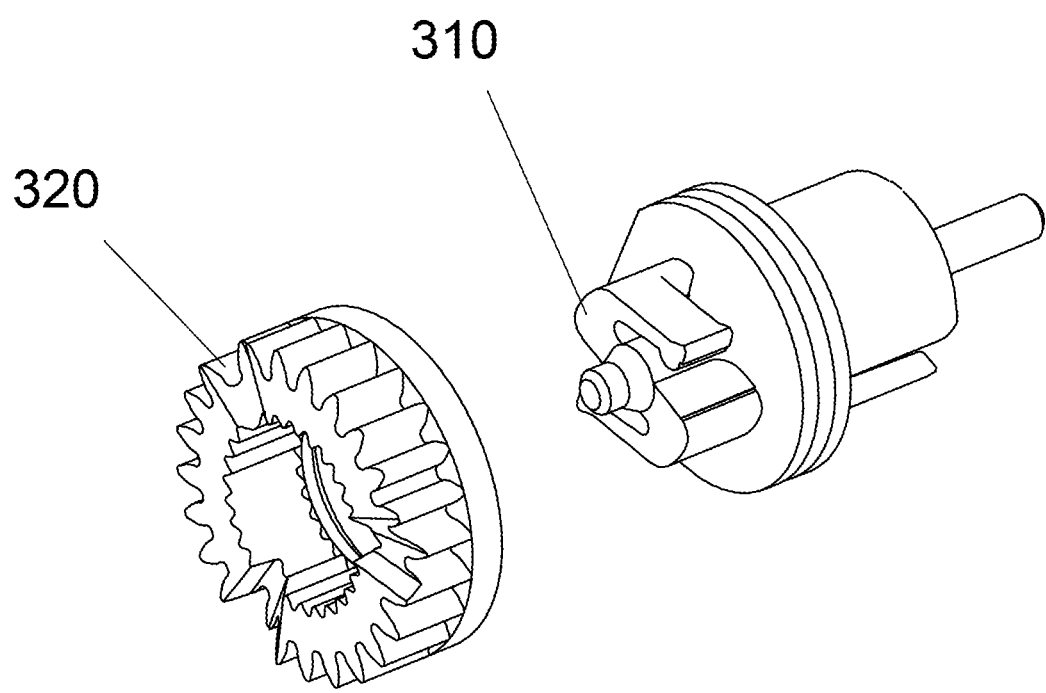

As tape is wound around the spool, the spool's diameter grows. This increases the surface speed of the spool relative to the tape still on the blister strip, creating tension since the blister strip is held by the hub. In order to avoid snapping of the tape, there may be a slip or detent clutch 300 provided on the peeling/spooling gear as shown in FIG. 3A to periodically release the tension and re-set the arrangement. The slip of the clutch is arranged to be less than the breaking strength of the backing tape but more than the peel strength of the tape. The slip clutch 300 is formed by z-shaped part 310, which rotates with the spool, and toothed ring portion 320 as shown in exploded form in FIG. 3B. Ring portion 320 is fixed relative to the inhaler so that z-shaped part 310 rotates incrementally inside it by slipping over the inner teeth of ring portion 320 one by one. Instead of a slip clutch, a flexible diameter spool or a tensioning arm could be provided.

Figure 4A:
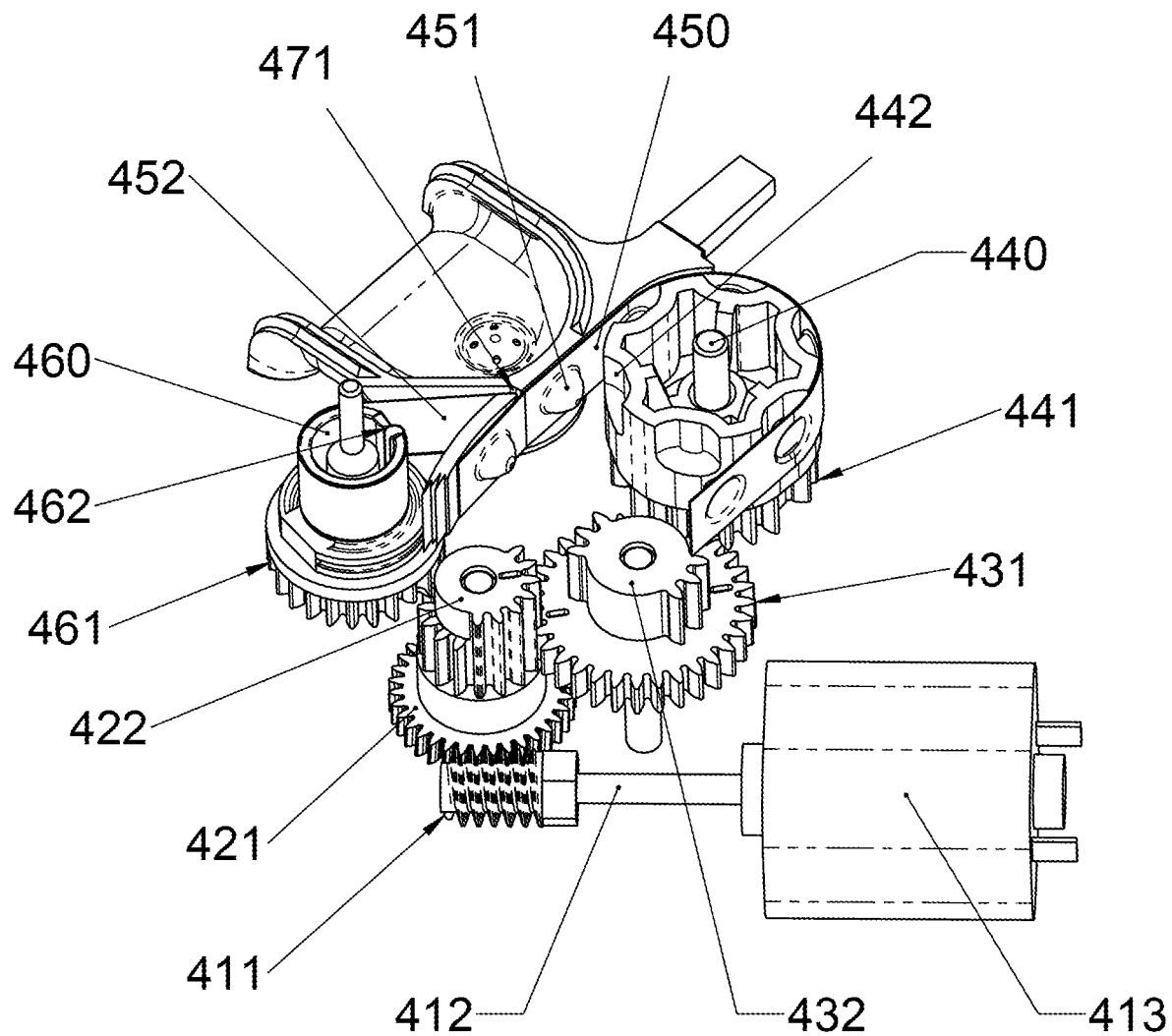
FIGS. 4A and 4B illustrate an example drive train.

FIG. 4A illustrates an example indexing gear train in full. A worm gear 411 is mounted on the output shaft 412 of a motor 413 such that the worm gear 411 rotates about its axis when the motor 413 is on. The worm gear 411 meshes with a first spur gear 421 such that first spur gear 421 rotates with worm gear 411. In an alternative example a spur gear could be used in place of the worm gear 411, e.g. being a spur bevel gear with teeth angled to mesh with first spur gear 421. A first sector gear 422 is mounted coaxially on the first spur gear 421 such that first sector gear 422 rotates with first spur gear 421. A second spur gear 431 meshes with the first sector gear 422 such that second spur gear 431 rotates with first sector gear 422 when a toothed part of the first sector gear 422 contacts the second spur gear 431. A second sector gear 432 is mounted coaxially on the second spur gear 431 such that the second sector gear 432 rotates with second spur gear 431. A third sector gear 441, having as many toothed portions as the to hub 440 has blister recesses (in the example shown, six), meshes with second sector gear 432 such that third sector gear 441 rotates with second sector gear 432 when toothed parts of the second and third sector gears 432 and 441 contact one another. The hub 440 is mounted coaxially on the third sector gear 441 such that the hub 440 rotates with the third sector gear 441.

FIG. 4A shows the location of the blister strip 450 at the point blister 451 is in the dosing position. Blister 451 of blister strip 450 is then moved into recess 442 of hub 440.

A spool 460 is mounted coaxially on a peeling/spooling gear 461 (which is a spur gear) such that spool 460 rotates with peeling/spooling gear 461. Peeling/spooling gear 461 meshes with first sector gear 422 such that peeling/spooling gear 461 rotates with first sector gear 422 when a toothed part of the first sector gear 422 contacts the peeling/spooling gear 461. A lip formed by the end of blister strip backing tape 452 is fed through a slot 471 in the outer wall of the blister strip track and affixed into slot 462 of spool 460. Such a lip could be reinforced to aid in slip through the slot 471, for example by the addition of a plastic layer or by doubling over of the backing material (which could, for example, be heat-sealed to itself). As backing tape 452 is peeled off each blister by rotation of spool 460 it slides around the peel edge of the slot 471.

Note that a gear, hub or spool being "mounted on", "carried on" or "sitting on" another gear such that the two rotate together may be achieved by the two being affixed together, permanently or reversibly (for example with one or more pins, nuts, bolts, screws, adhesives, clutches etc.) or by the two being integrally formed (for example as pieces of plastic or metal formed in a single mould). All of the gear pairs may be coupled in the same manner. Alternatively, one or more pairs of gears, for example first spur and sector gears 421 and 422 and third sector gear 441 and hub 440, may be integrally formed while one or more other pairs of gears, for example second spur and sector gears 431 and 432 and peeling/spooling gear 461 and spool 460, may be formed separately and subsequently coupled to rotate together.

Figure 4B:
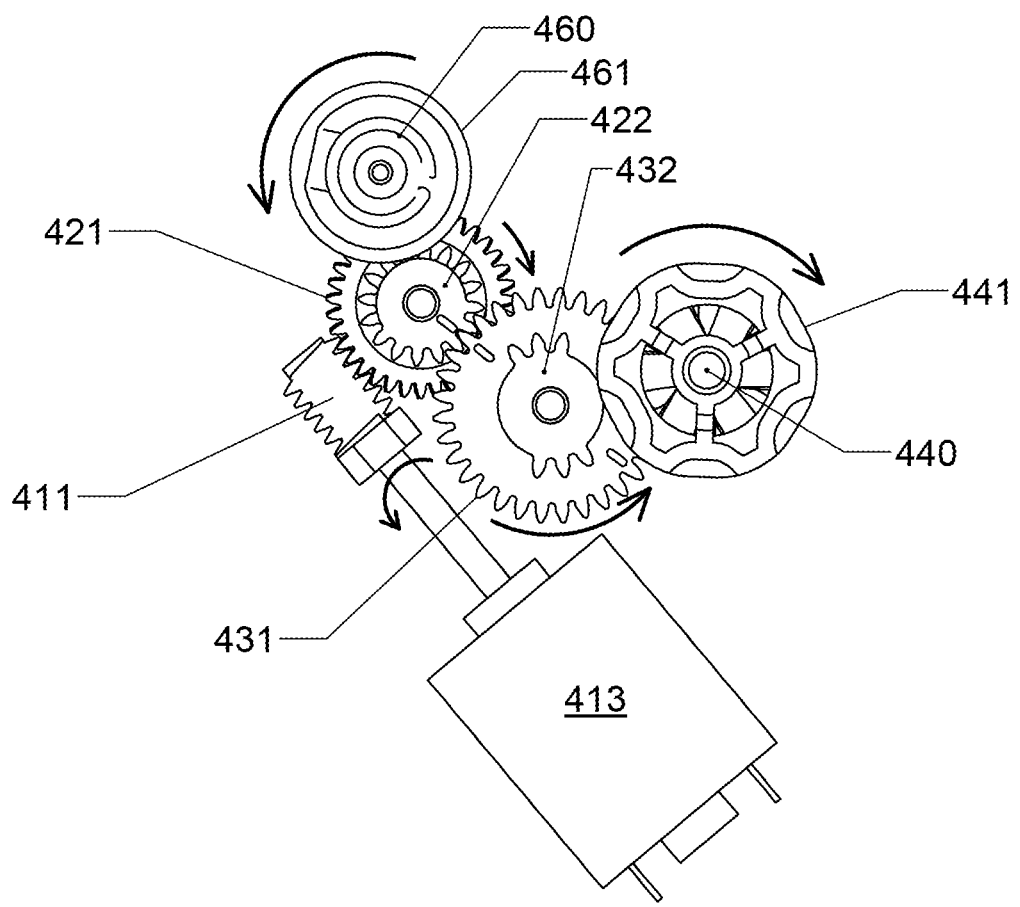

As shown in FIG. 4B, when motor 413 is on, output shaft 412 and therefore worm gear 411 rotate clockwise when viewed from worm gear end-on. This drives first spur gear 421 and therefore first sector gear 422 to rotate clockwise. This drives peeling/spooling gear 461 and therefore spool 460 to rotate anti-clockwise. The clockwise rotation of first sector gear 422 also drives the second spur gear 431 and therefore the second sector gear 432 to rotate anti-clockwise. This drives the third sector gear 441 and therefore the hub 440 to rotate clockwise. This drives the blister strip 450 to advance clockwise around the hub portion of the blister strip track.

Figure 5A:
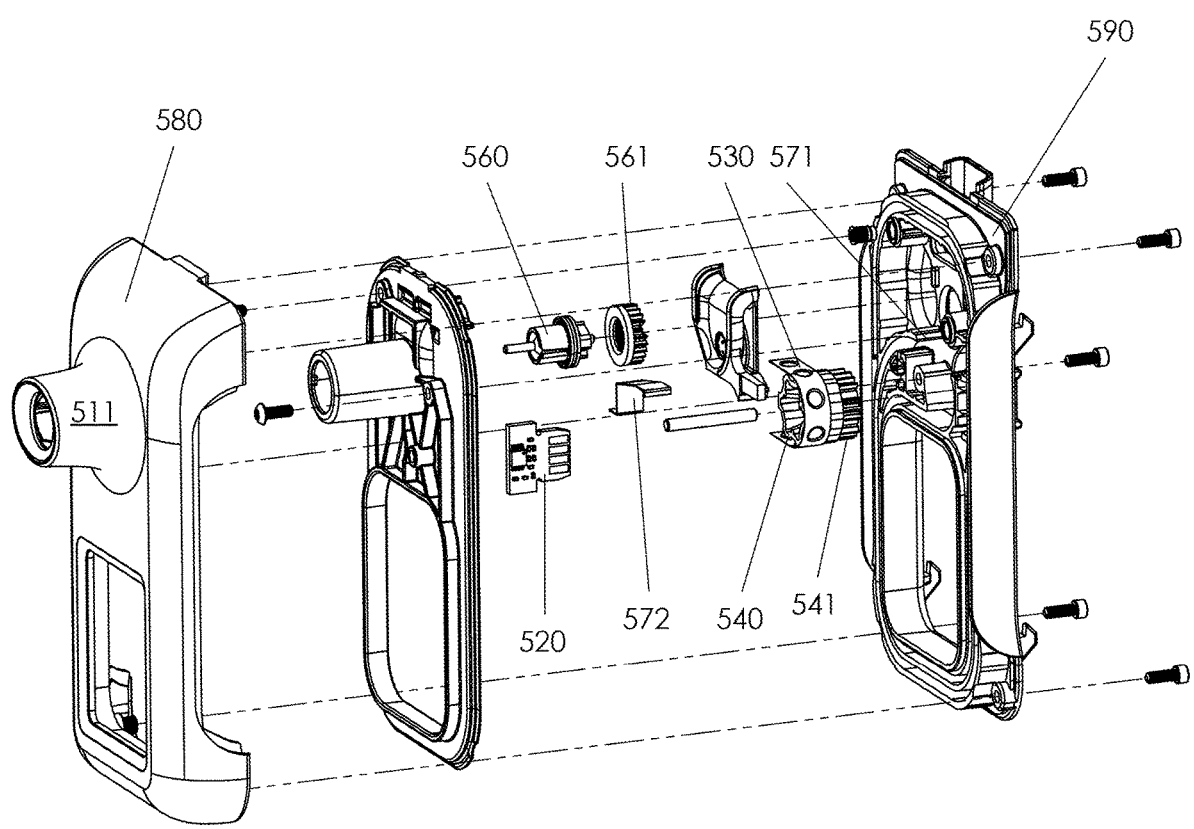
FIGS. 5A, 5B, 5C and 5D illustrate an example inhaler.

FIG. 5A is an exploded view of part of an example inhaler. A PCB (printed circuit board) 520, a third sector gear 541, a hub 540, a spool 560, a peeling/spooling gear 561, a slot 571 in the outer wall of the portion of the blister strip track curved around the hub and a spring finger 572 (for biasing the blister strip 530 such that the blister in the dosing position is pushed against the dose chamber opening) are all shown together with a cover 580, a base plate 590 and various axles for the gears and fastening means such as screws, nuts and bolts to hold the various layers of the inhaler together.

The inhaler may comprise a reusable inhaler body and a disposable blister strip cartridge. The inhaler body could for example comprise the dosing chamber, mouthpiece, motor, worm gear, indexing gear train (e.g. including the first and second spur gears, the first to third sector gears and the peeling/spooling gear), hub and spool while the cartridge could comprise the blister strip located in a track. This arrangement would minimise the cost of the cartridge.

Alternatively, one or more gears of the indexing drive train and/or the hub (or one or more gears of the indexing drive train and/or the motor) could be located in the cartridge. The drive means would then be disengaged from the hub whenever the cartridge is removed. This would prevent rotation of the hub by the motor when the cartridge is not in place.

As another option, the dosing chamber (together with a piezoelectric vibrator for pushing dry powder medicament into the mouthpiece) and mouthpiece could be included in the disposable part of the inhaler. This arrangement could be advantageous for reasons of hygiene, reducing the need to clean the mouthpiece and flow channel parts of the inhaler. It could also allow the inhaler body to be used by multiple patients, each attaching their own cartridge with their own mouthpiece and the drug prescribed for them.

Figure 5B:
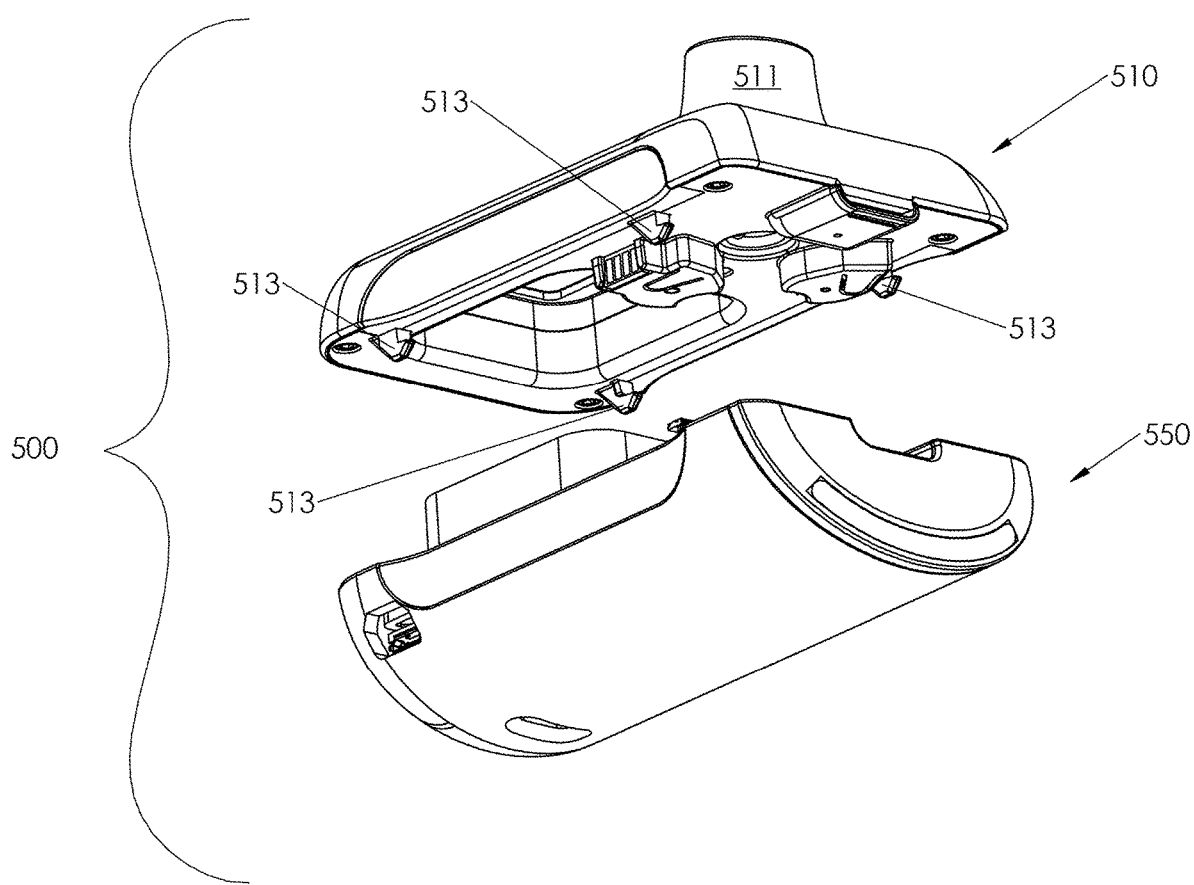
Figure 5C:
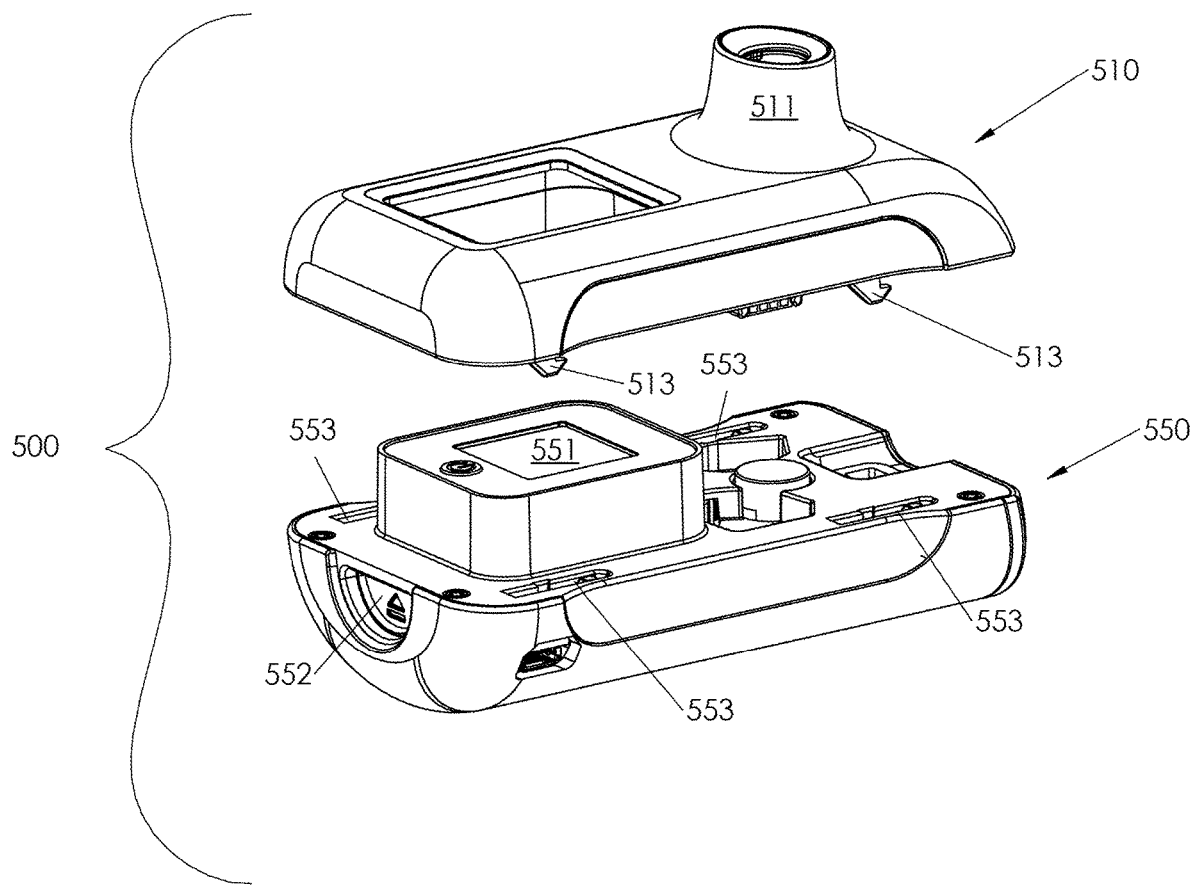
Figure 5D:
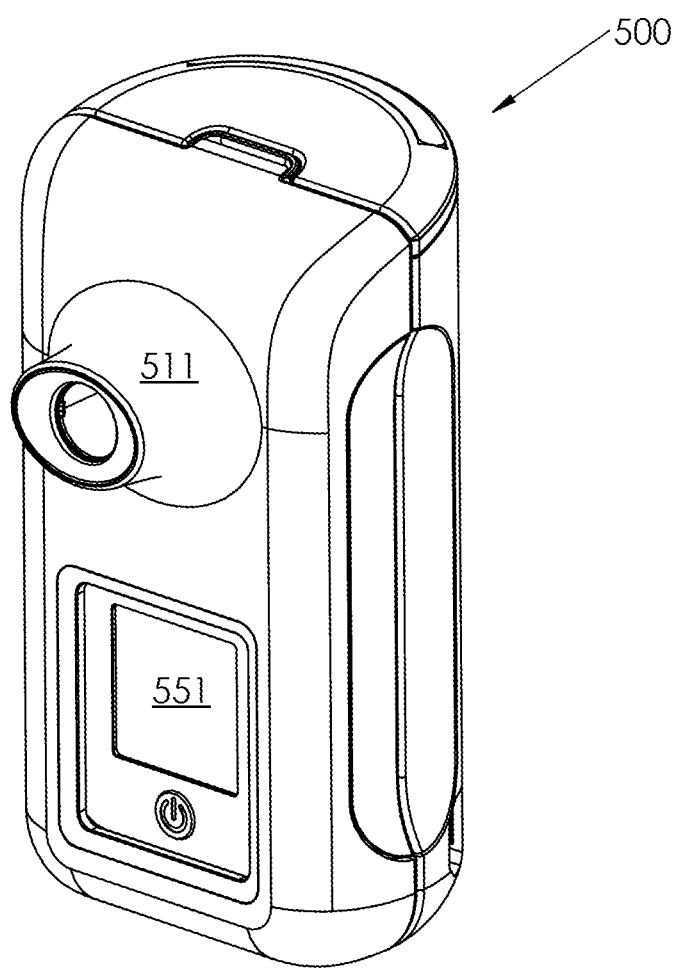

FIGS. 5B and 5C show an example replaceable cartridge inhaler 500 with a disposable cartridge 510 and a reusable part 550 separated, while FIG. 5D shows them joined together. Visible in FIGS. 5B to 5D are mouthpiece 511, display screen 551, cartridge release button 552, connector clips 513 and connector slots 553 into which connector clips 513 fit to join the cartridge to the reusable part.

Figure 6:
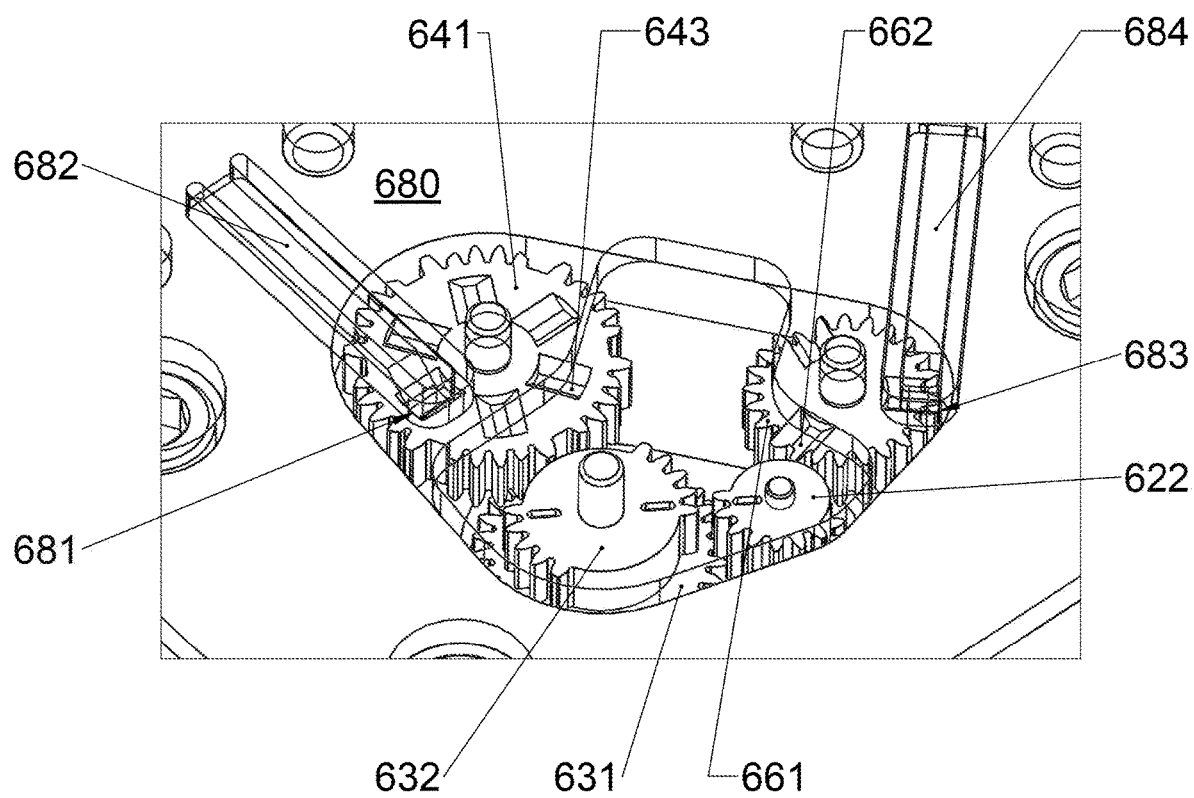
FIG. 6 illustrates an example detent arrangement.

In a cartridge-based inhaler with a design similar to that shown in FIG. 5A, when the cartridge is removed then the indexing drive train is free to rotate. This may not be desirable if there is any possibility of the cartridge being removed before it is empty, for example if multiple different cartridges (e.g. holding different types of medicament) can be attached to the inhaler body. For example a user may need to administer two or three different types of medicament each day and may do so using a single inhaler body onto which are swapped multiple different cartridges. Problems could arise in these circumstances since the hub may not be located with a recess in the dosing position, aligned with the dosing chamber, when a cartridge is attached to the inhaler body. FIG. 6 illustrates a means of solving this problem.

FIG. 6 shows a cover 680 on top of a first sector gear 622 (mounted on a first spur gear, not seen), a second spur gear 631, a second sector gear 632, a third sector gear 641 and a peeling/spooling gear 661.

The upper face of the third sector gear 641 as shown (i.e. the face over which the hub will be mounted) comprises recesses 643. The cover 680, which is fitted between the third sector gear 641 and the hub (not shown) comprises detent 681 on the distal end of spring arm 682. Spring arm 682 biases detent 681 down towards the upper face of the third sector gear 641. The detent 681 is located such that it sits in one of the recesses 643 when the hub is in one of its stopped positions (i.e. with a blister in the dosing position). The number of recesses 643 (in this example 6) corresponds to the number of blister recesses on the hub. Each time the blister strip is advanced by one blister, the detent 681 is forced upwards out of the recess 643 in which it has been residing and then snaps back down into the next recess 643 due to the biasing provided by the spring arm 682.

Similarly, the upper face of the peeling/spooling gear 661 as shown (i.e. the face over which the spool will be mounted) comprises recesses 662. The cover 680, which is fitted between the peeling/spooling gear 661 and the spool (not shown) comprises detent 683 on the distal end of spring arm 684. Spring arm 684 biases detent 683 down towards the upper face of the peeling/spooling gear 661. The detent 683 is located such that it sits in one of the recesses 662 when the spool is in one of its stopped positions (i.e. when a blister is in the dosing position). The number of recesses 662 (in this example 3) is set according to the ratio of the sizes of the third sector gear 641 and peeling/spooling gear 661 (in this example 2) and the number of blister recesses on the hub (in this example 6). Each time the blister strip is advanced by one blister, the detent 683 is forced upwards out of the recess 662 in which it has been residing and then snaps back down into the next recess 662 due to the biasing provided by the spring arm 684.

The strength of the biasing provided by the spring arms 682 and 684 and the sizes of the detents 681 and 683 and recesses 643 and 662 are arranged such that the drive means can generate sufficient force to index the gear train despite the detents, while the detents hold the drive train in place when disconnected from the drive means. This means that no complex position sensing is needed to establish the phase of the drive train on re-connection to the inhaler body since correct alignment is guaranteed. The power chosen for the motor should be balanced against the forces likely to be encountered during typical transportation and use of an inhaler. For example, drop tests could establish how strong the lock created by the spring arms and detents needs to be to prevent misalignment caused by the inhaler falling off a table or out of a pocket or handbag.

In addition, the detent arrangement on the third sector gear prevents any accidental rotation of the hub (for example as might be caused by the inhaler being dropped) while it is disengaged from the motor. Similarly, the detent arrangement on the peeling/spooling gear prevents any accidental rotation of the spool while it is disengaged from the motor (which could for example cause inadvertent unwinding of backing from the spool). These detent arrangements are therefore also useful in a non-cartridge based inhaler. The blister strip advance mechanism may include a blocking mechanism to prevent rotation of one or more gears in at least one direction. In some embodiments, the blocking mechanism comprises a recess on at least one gear configured to receive the detent. In other embodiments, the blocking mechanism includes the motor which resists rotation of the indexing gear train when the motor shaft is not rotating.

Figure 7A:
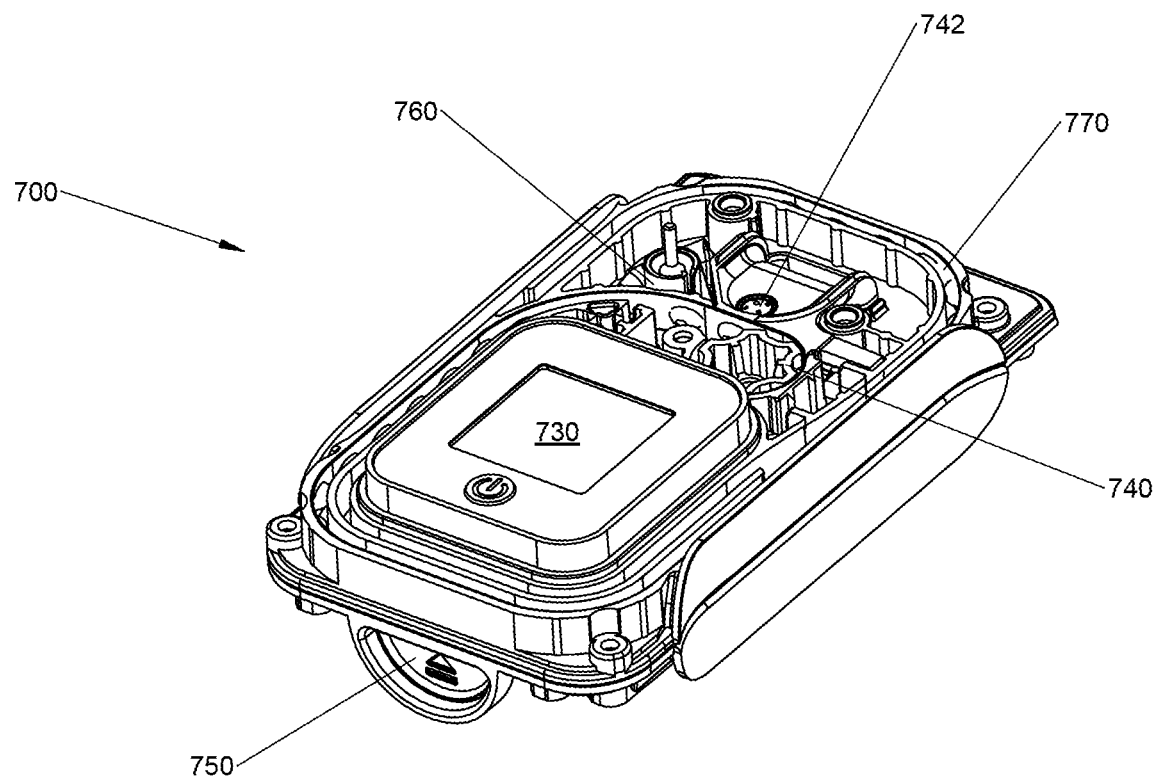
FIGS. 7A and 7B illustrate how an example blister strip advance mechanism could fit into an inhaler.

FIG. 7A illustrates how the blister strip advance mechanism could fit into an inhaler. Inhaler 700 is shown in FIG. 7A with outer housing 710 and mouthpiece cover 721 (both shown in FIG. 7B) removed. FIG. 7A shows a dosing chamber 742, display screen 730, hub 740, cartridge release button 750, spool 760 and blister strip track 770. Most of the blister strip track 770 is arranged close to the outer edge of the inhaler to maximise its length and therefore the number of doses per cartridge/disposable inhaler. The hub 740 and spool 760 are located in the space between the dosing chamber 742 and display screen 730.

Figure 7B:
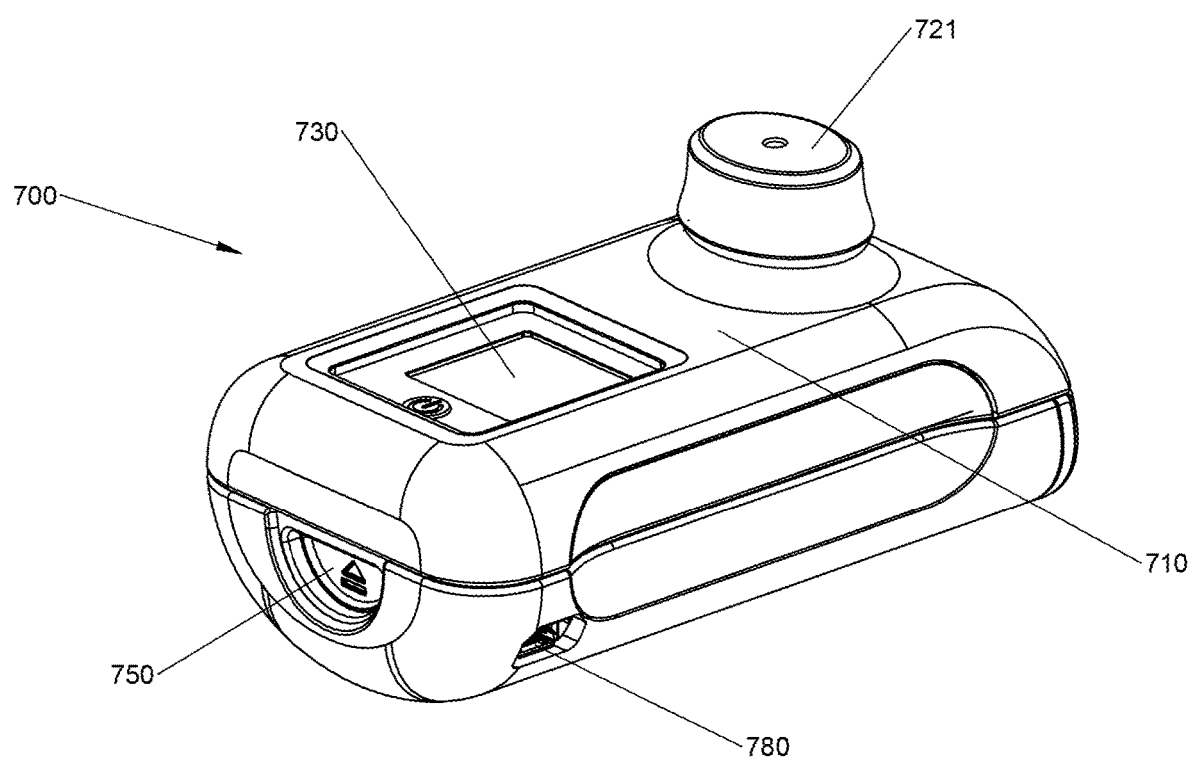

A charging socket 780 as shown in FIG. 7B may connect to a battery within the inhaler, for example located under display screen 730. A PCB may also be located under the display screen 730 in order to connect some or all of the display screen 730, charging socket 780, battery, motor and any other electronic components. For example, a switch could be provided close to the hub which cuts off power to the motor once a blister is successfully located in the dosing position. Such a switch could for example be mechanical, optical, or comprise a Hall effect sensor. User-actuated control means could be provided to re-start the motor when dose advancement is required. For example, display screen 730 could be a touch screen, a button or slider could be located on the exterior of the inhaler or an inhalation sensor somewhere in the flow channel comprising the mouthpiece and dosing chamber could detect when a user is inhaling through the mouthpiece in order to trigger the motor.

Figure 8:
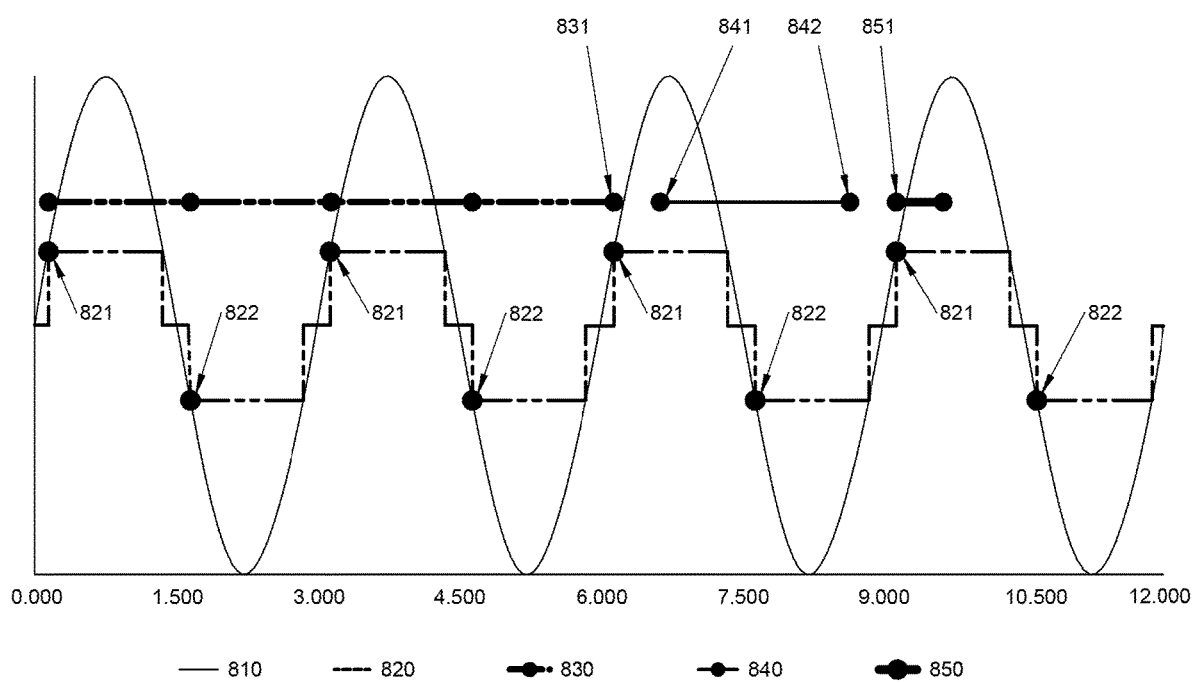
FIG. 8 shows an example airflow pattern with associated example sensor and control logic.

FIG. 8 illustrates the latter example used in a dry powder inhaler in which opened blisters are emptied by action of a piezoelectric vibrator. Sinusoid 810 is a trace of the airflow through the mouthpiece. Stepped square wave 820 shows the resulting airflow (e.g. digital pressure) sensor logic. Line 830 indicates the time period over which breathing pattern frequency is measured. (This may be done for example by a processor responsive to the sensor logic.) Line 840 indicates the time period over which a dose is advanced. Line 850 indicates the time period over which the piezo is vibrated. This may optionally be repeated over multiple, for example 4 to 12, e.g. 8, breath cycles. Points 821 indicate where inhalation is detected and points 822 indicate where exhalation is detected. At point 831 a processor verifies the user's breathing pattern is correct for dosing according to a comparison with some predetermined parameters and decides to deliver drug. At point 841 dose advance begins. At point 842 completion of dose advance is confirmed, for example using a photo gate. At 851 the piezo is fired. This could be timed to occur at a particular point during inhalation e.g. to maximise drug delivery to a particular section of the patient's airway.

Figure 9:
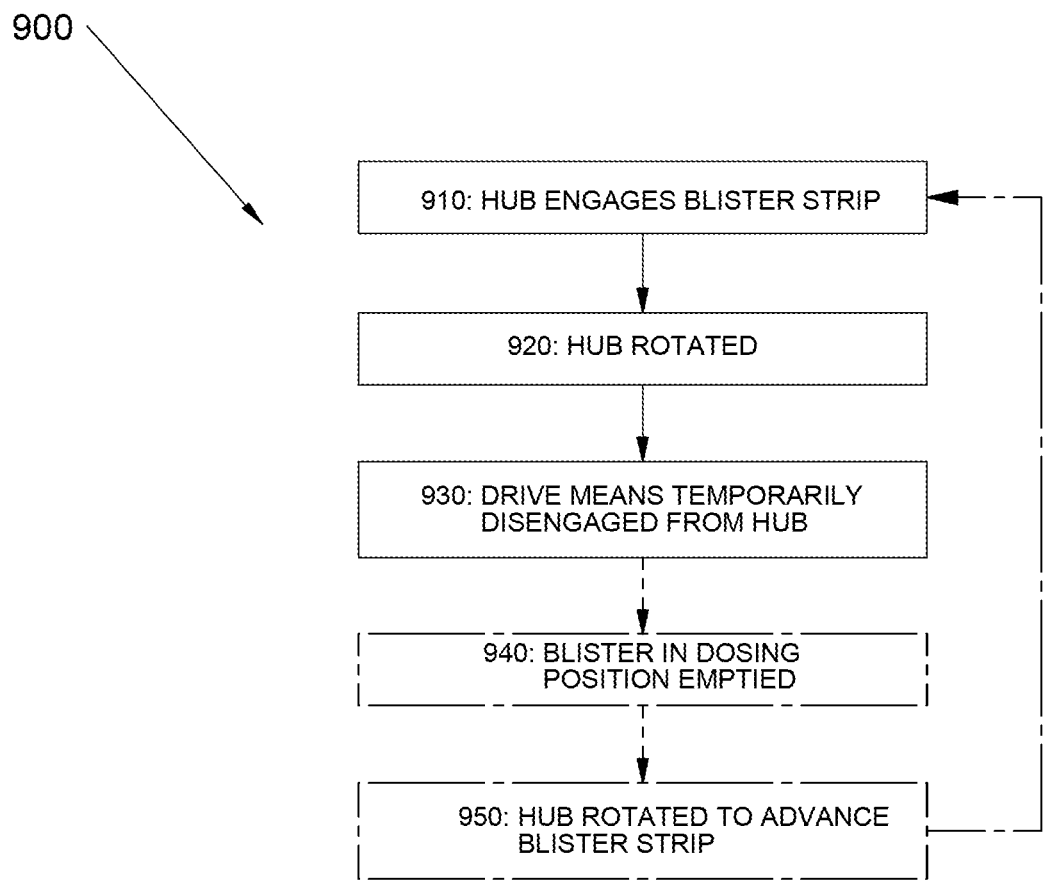
FIG. 9 is a flowchart of an example method.

FIG. 9 is a flowchart illustrating an example blister strip advance method 900. At 910 a recess of a hub engages a first, empty blister of the blister strip. At 920 the hub is rotated by means of an indexing gear train driven by drive means to move preceding second, full blister of the blister strip to a dosing position from which it can be emptied. At 930 the drive means is temporarily disengaged from the hub. At 940 the second blister in the dosing position is suitably emptied. Suitably, at 950 the hub is further rotated to advance the blister strip. The method may then suitably be repeated one or more times until every full blister of the blister strip has been emptied.

Figure 10:
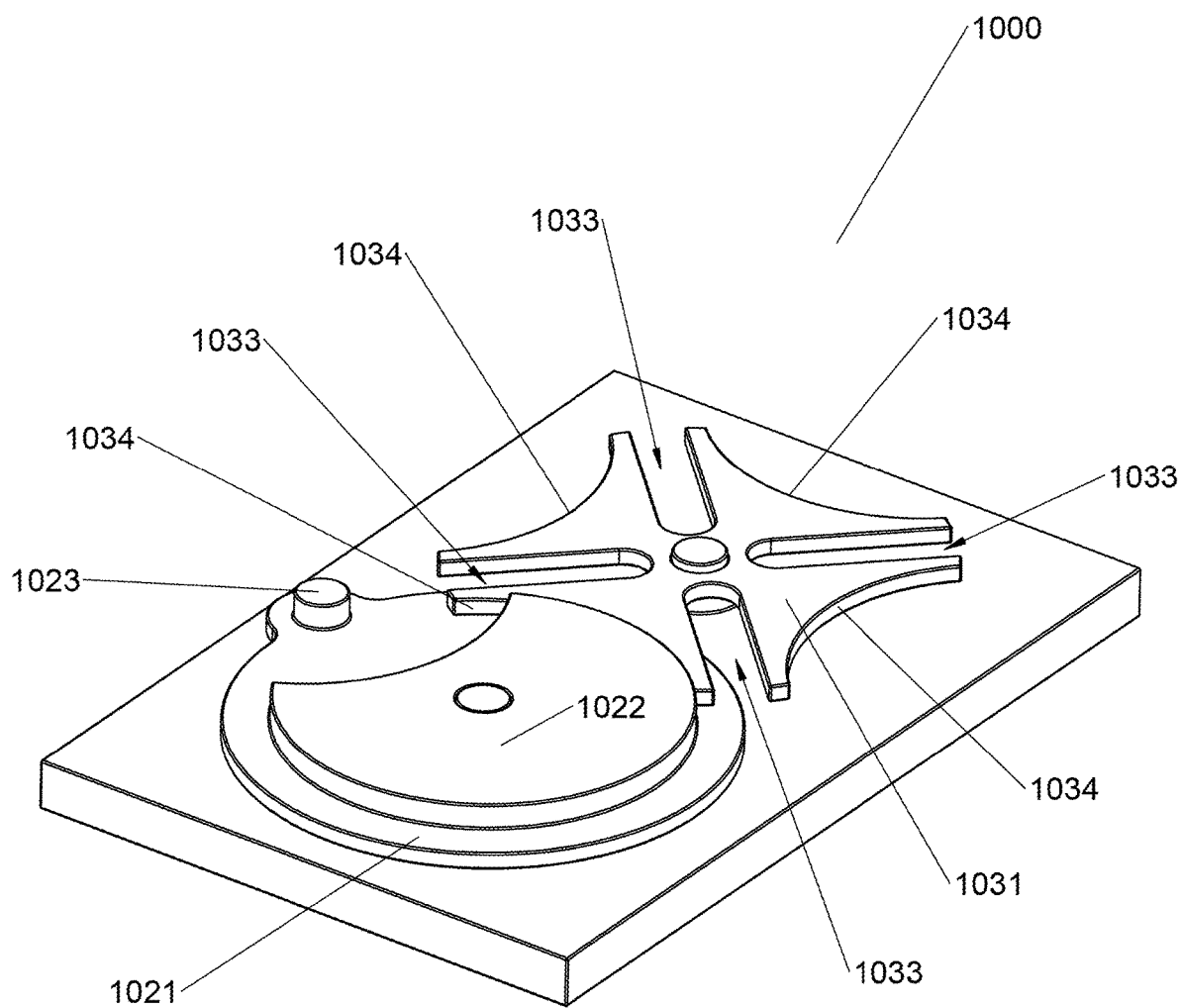
FIG. 10 illustrates an alternative example means for temporarily disengaging a hub from a drive means.

FIG. 10 illustrates a Geneva drive 1000; which could be used in place of a spur and sector gear arrangement to provide the temporary disengagement of the drive means from the hub. A sector gear 1022 is mounted on pin gear 1021, which carries pin 1023. Pin gear 1021 and sector gear 1022 are driven to rotate (directly or indirectly) by the drive means. When pin 1023 enters one of the slots 1033 in Maltese gear 1031, Maltese gear 1031 is driven to rotate. (It is free to do so since at this point it is not contacting sector gear 1022.) As pin gear 1021 rotates further, pin 1023 travels deeper into slot 1033, and then reverses direction relative to the slot until it emerges from the mouth of the slot again. By the time this occurs, sector gear 1022 is again contacting one of the recesses 1034 in the Maltese gear, blocking any further rotation. The Maltese gear thus undergoes indexed rotation. If the recesses 1034 are shaped to receive blisters, the Maltese gear could be the hub.

The above description relates to exemplary uses of the invention, but it will be appreciated that other implementations and variations are possible.

In addition, the skilled person can modify or alter the particular geometry and arrangement of the particular features of the apparatus. Other variations and modifications will also be apparent to the skilled person. Such variations and modifications can involve equivalent and other features which are already known and which can be used instead of, or in addition to, features described herein. Features that are described in the context of separate embodiments can be provided in combination in a single embodiment. Conversely, features which are described in the context of a single embodiment can also be provided separately or in any suitable sub-combination.

What is claimed is:

1. A blister strip advance mechanism comprising:
    an indexing gear train comprising a plurality of gears;
    drive means comprising a motor configured to drive said indexing gear train; and
    a hub comprising a recess shaped to engage a first blister of a blister strip, said hub being rotatable by the indexing gear train to engage the first blister in said recess and move the engaged blister strip such that a second blister of the blister strip is moved to a dosing position, wherein the second blister is configured to be emptied when the second blister is in the dosing position;
    wherein the indexing gear train is configured to temporarily disengage said drive means comprising the motor from the hub when the second blister is in said dosing position such that the hub ceases rotation during the temporary disengagement while the drive means comprising the motor continues to drive the indexing gear train, and wherein each gear of the plurality of gears of the indexing gear train rotates in a single gear rotation direction, and wherein the blister strip advance mechanism includes a blocking mechanism for preventing each gear of the plurality of gears of the indexing gear train from rotating in a direction opposite to the gear rotation direction.

2. The blister strip advance mechanism of claim 1, wherein the plurality of gears of the indexing gear train includes a sector gear.

3. The blister strip advance mechanism of claim 2, wherein the plurality of gears of the indexing gear train further includes a spur gear, the hub being arranged to be driven by said spur gear, the spur gear being arranged to be driven by said sector gear and the sector gear being arranged to be driven by the drive means.

4. The blister strip advance mechanism of claim 2, wherein said sector gear comprises a blocking disc of a Geneva drive and said hub comprises a Maltese gear of the Geneva drive.

5. The blister strip advance mechanism of claim 4, wherein the blocking disc comprises a pin, and wherein the Maltese gear comprises at least one slot such that the hub is configured to be rotated by the blocking disc of the Geneva drive when the pin of the blocking disc enters the at least one slot of the Maltese gear of the hub.

6. The blister strip advance mechanism of claim 1, wherein the hub is further rotatable by the indexing gear train to release the first blister.

7. The blister strip advance mechanism of claim 6, wherein the hub is further rotatable by the indexing gear train to engage the second blister.

8. The blister strip advance mechanism of claim 7, further comprising a track, wherein the blister strip has a leading end and a trailing end, and wherein the blister strip is configured to move through said track;
part of said track passing around part of a circumference of the hub such that the second blister is engaged by the hub when the blister strip is in the track and the second blister is aligned with the hub;
the track being shaped such that, as the blister strip is advanced, the leading end of the blister strip moves into a part of the track vacated by the trailing end of the blister strip.

9. The blister strip advance mechanism of claim 1, further comprising a spooling gear carrying a spool arranged to rotate therewith, wherein an end of a backing strip of the blister strip is configured to be affixed to the spool;
said spooling gear being configured to be rotated by the plurality of gears of the indexing gear train substantially concurrently with the hub such that backing is peeled off the second blister as the second blister is moved into the dosing position, arrival of the second blister at the dosing position being substantially coincident with completion of peeling of backing from the second blister.

10. The blister strip advance mechanism of claim 9, wherein the plurality of gears of the indexing gear train includes a sector gear, and the plurality of gears of the indexing gear train further includes a spur gear, the hub being arranged to be driven by said spur gear, the spur gear being arranged to be driven by said sector gear and the sector gear being arranged to be driven by the drive means, and wherein the spooling gear is arranged to be driven by the sector gear.

11. The blister strip advance mechanism of claim 9, wherein the spooling gear is arranged with respect to the hub such that, in operation, backing is peeled off the second blister at an angle of between 40 and 140 degrees.

12. The blister strip advance mechanism of claim 9, further comprising a slip clutch on the spooling gear.

13. The blister strip advance mechanism of claim 1, wherein the plurality of gears of the indexing gear train includes:
a worm gear carried on an output shaft of the drive means and arranged to rotate therewith;
a first spur gear meshing with said worm gear;
a first sector gear carried on said first spur gear and arranged to rotate therewith;
a second spur gear meshing with said first sector gear;
a second sector gear carried on said second spur gear and arranged to rotate therewith; and
a third sector gear meshing with said second sector gear;
wherein the hub is carried on the third sector gear and is arranged to rotate therewith.

14. The blister strip advance mechanism of claim 13, further comprising:
a spooling gear carrying a spool arranged to rotate therewith, wherein an end of a backing strip of the blister strip is configured to be affixed to the spool; said spooling gear being configured to be rotated by the indexing gear train substantially concurrently with the hub such that backing strip is peeled off the second blister as the second blister is moved into the dosing position, arrival of the second blister at the dosing position being substantially coincident with completion of peeling of backing strip from the second blister, and wherein the spooling gear is a third spur gear meshing with the first sector gear.

15. The blister strip advance mechanism of claim 1, further comprising one or more detents arranged to hold the indexing gear train in position when the indexing gear train is disengaged from the drive means.

16. A dosing mechanism comprising:
the blister strip advance mechanism of claim 1; and
a dosing chamber comprising two openings, the dosing position being aligned with one of said openings such that contents of the blister in the dosing position can only exit the blister via said dosing chamber.

17. An inhaler comprising the dosing mechanism of claim 16.

18. The inhaler of claim 17, comprising an inhaler body and a replaceable blister strip cartridge, said inhaler body comprising the dosing chamber, the drive means, the indexing gear train and the hub, and said replaceable blister strip cartridge comprising the blister strip.

19. The blister strip advance mechanism of claim 1, wherein the second blister is disengaged from the hub when the second blister is in the dosing position, and
wherein the hub is further rotatable by the indexing gear train such that the hub engages the second blister.

20. The blister strip advance mechanism of claim 1, wherein the plurality of gears of the indexing gear train includes a first gear that rotates in a first gear rotation direction and a second gear that rotates in a second gear rotation direction, the first gear rotation direction being different than the second gear rotation direction.

21. The blister strip advance mechanism of claim 1, wherein the blocking mechanism comprises a recess on at least one gear of the plurality of gears of the indexing gear train configured to receive a detent, the detent at least temporarily preventing rotation of the at least one gear when the detent is in the recess.

22. The blister strip advance mechanism of claim 1, wherein the motor comprises an electrical motor having a motor shaft and the blocking mechanism comprises the motor shaft, the motor configured to drive the indexing gear train such that each gear of the plurality of gears rotates in a single gear rotation direction when the motor shaft is rotating and the motor shaft resists rotation of the indexing gear train when the motor shaft is not rotating.

23. A method for advancing a blister strip comprising:
engaging a first blister of said blister strip in a recess of a hub;
rotating said hub by an indexing gear train driven by a motor including an output shaft to move a second blister of the blister strip to a dosing position at which said second blister can be emptied; and
temporarily disengaging said motor from said hub when the second blister is in said dosing position with the indexing gear train such that the hub ceases rotation during the temporary disengagement while the motor continues to drive the indexing gear train,
wherein, the indexing gear train comprises a plurality of gears, and wherein each gear of the plurality of gears rotates in a single direction, and
wherein a blocking mechanism is coupled to the indexing gear train and the method includes preventing rotation of each gear of the plurality of gears of the indexing gear train in a direction opposite to the gear rotation direction by the blocking mechanism.

24. The method of claim 23, further comprising:
further rotating the hub by the indexing gear train to release the first blister and engage the second blister of the blister strip, wherein the blister strip has a leading end and a trailing end such that the leading end of the blister strip moves into a part of a track, through which said blister strip is moving, already vacated by the trailing end of the blister strip as the blister strip advances;
wherein part of said track passes around part of a circumference of the hub such that the first blister is engaged by the hub when the blister strip is in the track.

25. The method of claim 23, further comprising the indexing gear train rotating a spooling gear carrying a spool arranged to rotate therewith and to which an end of a backing strip of the blister strip is affixed;
said rotation of said spooling gear being substantially concurrent with said rotation of the hub such that the backing is peeled off the second blister as the second blister is moved into the dosing position, and arrival of the second blister at the dosing position being substantially coincident with completion of peeling of the backing from the second blister.

26. The method of claim 23, further comprising rotating an output shaft of the motor such that a worm gear carried on said output shaft rotates therewith;
such that a first spur gear meshing with said worm gear rotates therewith;
such that a first sector gear carried on said first spur gear rotates therewith;
such that a second spur gear meshing with said first sector gear rotates therewith;
such that a second sector gear carried on said second spur gear rotates therewith;
such that a third sector gear meshing with said second sector gear rotates therewith;
such that the hub, being carried on the third sector gear, rotates therewith.

27. The method of claim 26, further comprising the indexing gear train rotating a spooling gear carrying a spool arranged to rotate therewith and to which an end of a backing strip of the blister strip is affixed;
said rotating of said spooling gear being substantially concurrent with said rotating of the hub such that the backing strip is peeled off the second blister as the second blister is moved into the dosing position, and arrival of the second blister at the dosing position being substantially coincident with completion of peeling of the backing strip from the second blister, and wherein the spooling gear is a third spur gear meshing with the first sector gear.

28. A method for dosing a dry powder medicament, comprising:
the method of claim 23; and
emptying contents of the second blister into a dosing chamber comprising two openings, the dosing position being aligned with one of said openings such that contents of the second blister in the dosing position can only exit the second blister via said dosing chamber.

29. A blister strip advance mechanism comprising:
a drive means;
an indexing gear train configured to be driven by said drive means, said indexing gear train comprising:
a worm gear carried on an output shaft of the drive means and arranged to rotate therewith;
a first spur gear meshing with said worm gear;
a first sector gear carried on said first spur gear and arranged to rotate therewith;
a second spur gear meshing with said first sector gear;
a second sector gear carried on said second spur gear and arranged to rotate therewith; and
a third sector gear meshing with said second sector gear;
a hub carried on the third sector gear and arranged to rotate therewith, said hub comprising a recess shaped to engage a first blister of a blister strip, said hub being rotatable by the indexing gear train to engage the first blister in said recess and move the engaged blister strip such that a second blister of the blister strip is moved to a dosing position, wherein the second blister is configured to be emptied when the second blister is in the dosing position; and
a spooling gear comprising a third spur gear meshing with the first sector gear, the spooling gear carrying a spool arranged to rotate therewith, wherein an end of a backing strip of the blister strip is configured to be affixed to the spool,
wherein said spooling gear is configured to be rotated by the indexing gear train substantially concurrently with the hub such that backing is peeled off the second blister as the second blister is moved into the dosing position, arrival of the second blister at the dosing position being substantially coincident with completion of peeling of backing from the second blister.

30. A blister strip advance mechanism comprising:
an indexing gear train;
drive means comprising a motor configured to drive said indexing gear train; and
a hub comprising a recess shaped to engage a first blister of a blister strip, said hub being rotatable by the indexing gear train to engage the first blister in said recess and move the engaged blister strip such that a second blister of the blister strip is moved to a dosing position, wherein the second blister is configured to be emptied when the second blister is in the dosing position;

wherein the indexing gear train is configured to temporarily disengage said drive means comprising the motor from the hub when the second blister is in said dosing position;

wherein the indexing gear train comprises a sector gear; and wherein the sector gear comprises a blocking disc of a Geneva drive and said hub comprises a Maltese gear of the Geneva drive.

31. A blister strip advance mechanism comprising:
an indexing gear train comprising:
   a worm gear carried on an output shaft of the drive means and arranged to rotate therewith;
   a first spur gear meshing with said worm gear;
   a first sector gear carried on said first spur gear and arranged to rotate therewith;
   a second spur gear meshing with said first sector gear;
   a second sector gear carried on said second spur gear and arranged to rotate therewith; and
   a third sector gear meshing with said second sector gear;
drive means comprising a motor configured to drive said indexing gear train; and
a hub comprising a recess shaped to engage a first blister of a blister strip, said hub being rotatable by the indexing gear train to engage the first blister in said recess and move the engaged blister strip such that a second blister of the blister strip is moved to a dosing position, wherein the second blister is configured to be emptied when the second blister is in the dosing position;
wherein the hub is carried on the third sector gear and is arranged to rotate therewith; and
wherein the indexing gear train is configured to temporarily disengage said drive means comprising the motor from the hub when the second blister is in said dosing position.

32. The blister strip advance mechanism of claim 31, wherein the hub is further rotatable by the indexing gear train to release the first blister.

33. The blister strip advance mechanism of claim 32, wherein the hub is further rotatable by the indexing gear train to engage the second blister.

34. The blister strip advance mechanism of claim 33, further comprising a track, wherein the blister strip has a leading end and a trailing end, and wherein the blister strip is configured to move through said track;
part of said track passing around part of a circumference of the hub such that the second blister is engaged by the hub when the blister strip is in the track and the second blister is aligned with the hub;
the track being shaped such that, as the blister strip is advanced, the leading end of the blister strip moves into a part of the track vacated by the trailing end of the blister strip.

35. The blister strip advance mechanism of claim 31, further comprising:
a spooling gear carrying a spool arranged to rotate therewith, wherein an end of a backing strip of the blister strip is configured to be affixed to the spool;
said spooling gear being configured to be rotated by the indexing gear train substantially concurrently with the hub such that backing is peeled off the second blister as the second blister is moved into the dosing position, arrival of the second blister at the dosing position being substantially coincident with completion of peeling of backing from the second blister.

36. The blister strip advance mechanism of claim 35, wherein the spooling gear is arranged with respect to the hub such that, in operation, backing is peeled off the second blister at an angle of between 40 and 140 degrees.

37. The blister strip advance mechanism of claim 35, further comprising a slip clutch on the spooling gear.

38. The blister strip advance mechanism of claim 31, further comprising one or more detents arranged to hold the indexing gear train in position when the indexing gear train is disengaged from the drive means.

39. A dosing mechanism comprising:
the blister strip advance mechanism of claim 31; and
a dosing chamber comprising two openings, the dosing position being aligned with one of said openings such that contents of the blister in the dosing position can only exit the blister via said dosing chamber.

40. An inhaler comprising the dosing mechanism of claim 39.

41. The inhaler of claim 40, comprising an inhaler body and a replaceable blister strip cartridge, said inhaler body comprising the dosing chamber, the drive means, the indexing gear train and the hub, and said replaceable blister strip cartridge comprising the blister strip.

* * * * *